United States Patent [19]

Hecht

[11] Patent Number: 5,519,126

[45] Date of Patent: May 21, 1996

[54] OLIGONUCLEOTIDE N-ALKYLPHOSPHORAMIDATES

[75] Inventor: Sidney M. Hecht, Charlottesville, Va.

[73] Assignee: University of Virginia Alumni Patents Foundation, Charlottesville, Va.

[21] Appl. No.: 155,648

[22] Filed: Nov. 22, 1993

Related U.S. Application Data

[63] Continuation of Ser. No. 975,972, Nov. 13, 1992, abandoned, which is a continuation of Ser. No. 837,616, Feb. 21, 1992, abandoned, which is a continuation of Ser. No. 702,112, May 16, 1991, abandoned, which is a continuation of Ser. No. 508,522, Apr. 11, 1990, abandoned, which is a continuation of Ser. No. 173,053, Mar. 25, 1988, abandoned.

[51] Int. Cl.$^6$ .................. C07H 21/02; C07H 21/00; C07H 21/04
[52] U.S. Cl. .................. 536/24.3; 536/24.1; 536/25.6
[58] Field of Search ............... 536/24.3, 25.32, 536/25.34, 28.1, 25.6

[56] References Cited

U.S. PATENT DOCUMENTS

| | | | |
|---|---|---|---|
| 4,378,458 | 3/1983 | Gohlke et al. | 536/26.6 |
| 4,500,707 | 2/1985 | Caruthers et al. | 536/25.4 |
| 4,547,569 | 10/1985 | Letsinger et al. | 536/25.32 |
| 4,563,417 | 1/1986 | Albarella et al. | 435/6 |
| 4,582,789 | 4/1986 | Sheldon, III et al. | 435/6 |
| 4,605,735 | 8/1986 | Miyoshi et al. | 536/26.3 |
| 4,725,677 | 2/1988 | Koster et al. | 536/25.34 |

FOREIGN PATENT DOCUMENTS 0169787  1/1986  European Pat. Off.

OTHER PUBLICATIONS

Thuong et al. (1985) Biochimie vol. 67: 673–684.

Uhlmann et al. (1990) Chemical Review vol. 90(4): 544–579.

*Primary Examiner*—Nancy T. Vogel
*Attorney, Agent, or Firm*—Oblon, Spivak, McClelland, Maier & Neustadt

[57] ABSTRACT

Oligonucleotide N-alkylphosphoramidates useful for combatting diseases by biochemical intervention at the RNA and DNA level are disclosed.

1 Claim, 5 Drawing Sheets

OLIGONUCLEOTIDE N-ALKYLPHOSPHORAMIDATES

This is a continuation of Ser. No. 07/975,972, now abandoned, filed on Nov. 13, 1992, which is a continuation of application Ser. No. 07/837,616, now abandoned, filed Feb. 21, 1992, which is a continuation of application Ser. No. 07/702,112, now abandoned, filed May 16, 1991, which is a continuation of application Ser. No. 07/508,522, now abandoned, filed Apr. 11, 1990, which is a continuation of application Ser. No. 07/173,053, now abandoned, filed Mar. 25, 1988, all now abandoned.

BACKGROUND OF THE INVENTION

1. Field of the Invention

The invention relates to substances which have the ability to bind to polynucleotides, e.g. DNA or RNA.

2. Discussion of the Background

Inhibition of the expression of single proteins by polynucleotides complementary to their mRNA's ("antisense mRNA's") is well documented (see, e.g., Izant and Weintraub, 1984; Rosenberg et al, 1985). This technique has even been employed for the differential deletion of the expression of a single protein within an operon (Pestka et al, 1984).

While this technique is best suited to in vitro studies, given the difficulties of delivering large oligonucleotides into intact cells and stabilizing them against metabolic degradation once they are introduced, Zamecnik and Stephenon have reported the use of an oligonucleotide (d(AATG-GTAAAATGG)) complementary to the reiterated terminal sequences of Rous Sarcoma virus to inhibit the replication of the intact virus (Zamecnik and Stephenson, 1978, Stephenson and Zamecnik, 1978).

A number of laboratories have also investigated the feasibility of utilizing the polynucleotide probes to destroy their complementary target sequences by modifying the probes to contain attached alkylating agents (Vlassov et al, 1985; Norre et al., 1985a,b; Zarytova et al, 1986; Iverson and Dervan, 1987) or prosthetic groups that mediate the generation of diffusible oxygen radicals (Dreyer and Dervan, 1985; Chu and Orgel, 1985; Vlassov et al., 1985b; Boidot-Forge et al., 1986).

There are several problems with the use of such probe molecules for therapeutic intervention, or even for mechanistic studies. The change in free energy required for duplex formation argues that at least 12 nucleotides (and perhaps as many as 20) might be required for stable binding of a probe oligonucleotide to its target sequence (Naylor and Gilham, 1986; Mevarech et al., 1973, Noyes et al., 1979). Duplex formation is reversible and could also involve (transient) complex formation with sequences partially complementary to the probe (Wallace et al., 1979; Itakura and Riggs, 1980; Conner et al., 1983). This problem becomes more serious as the length of the probe is increased.

Additional problems also include the following. (1) Oligonucleotides are readily susceptible to degradation by nuclease activities present in all cells. (2) The delivery of unmodified oligonucleotides across cell membranes with reasonable efficiency is complicated by the negatively charged phosphate oxygen anions on the oligonucleotides. (3) The reactive groups employed thus far to permit a probe oligonucleotide to destroy their target sequences are such that they can also mediate destruction of the probes. (4) The chemical processes employed to date for destruction of target sequences are all limited to a single event (alkylating agents) or are unselective and probably unattainable under physiologic conditions.

In 1981, Letsinger and Schott described the preparation of a phenanthridinium TpT derivative (1) and demonstrated that it had an affinity for single-stranded poly A much greater than that of TpT itself. The mode of interaction of the modified dinucleotide with poly A was suggested to involve, in addition to Watson-Crick base pairing, both intercalation of the phenanthridine moiety and ionic interaction of one of the positively charged intercalator amino groups with the phosphate oxygen anion on poly A.

The work of Letsinger and Schott has been extended in the laboratory of C. Helene. First, these workers have demonstrated that the presence of an intercalator at the end of a probe oligonucleotide results in target sequence affinity at least as great as when the intercalator is tethered within the probe sequence.

Second, they demonstrated that the intercalator could be modified to mediate cleavage of the target strand, and would do so more efficiently under conditions where the probe was actually bound to the target (Doan, 1986). Unfortunately, the specific system developed was inefficient both for target binding and cleavage, and cannot be adapted to function under physiological conditions.

The third finding of this group is that oligonucleotide probes modified with intercalators can bind to mRNA's selectively in cell free systems and in Xenopus oocytes and thereby block translation of the derived proteins (Helene et al., 1985; Toulme et al., 1986; Cazenave et al., 1986.)

The issues of cell permeability and intracellular stability have been addressed by Miller and Ts'o. These workers have prepared oligonucleotides containing methylphosphonate linkages rather than the normal phosphodiester linkages in RNA and DNA (Miller et al., 1983a,b). Oligonucleotide analogs containing these linkages have been shown by Miller and Ts'o to

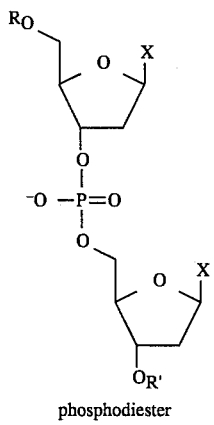

phosphodiester

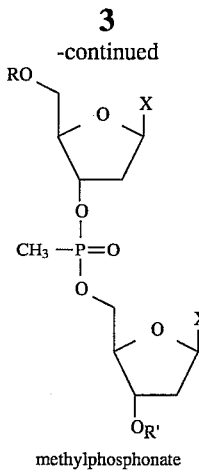

methylphosphonate be permeable to mammalian cells and to block mRNA production (Murakami et al., 1985, Blake et al., 1985a,b; Miller et al., 1985; Agris et al., 1986).

While the studies described by Miller and Ts'o are encouraging in it must be noted that this work also has limitations, which include:

the observation that the probe oligonucleotides could block mRNA translation only when they were complementary to the 5'-end or initiation codon regions of the mRNA (Blake et al., 1985a,b);

the fact that the modified oligonucleotides are all complex mixtures of diastereomers due to the presence of chirality at the phosphonate P's ($2^{n-1}$ isomers for an oligonucleotide n residues in length), each of which can be anticipated to have unique binding characteristics for the target RNA sequence (Pramanik and Kan, 1987).

Letsinger et al, "Nucleic Acids Research", vol. 14, no. 8, pp. 3487–3499 (1986), have described the contribution of certain lipophilic blocking group to polynucleotide affinity by probe molecules. This publication discloses several synthetic analogues of d-ApA containing a bulky lipophilic group (2,2,2-trichloroethoxy or 2,2,2-trichloro- 1,1-dimethylethoxy), a small uncharged hydrogen-bonding group (amido), or a cationic phosphoramidate (2-aminoethylamido, protonated in neutral aqueous media).

Letsinger et al's study however fails to identify any relationship between the length/lipophilicity of the alkyl chain and the oligonucleotide binding properties of the probe, provides no teaching as to the molecular basis for the observed effects, does not identify ways to enhance/utilize the probe for biochemical intervention, and does not identify oligonucleotide N-alkylphosphoramidates as a discrete class of molecules with potentially useful properties.

There is therefore a need for a class of compounds which are capable of transport across cellular membrane, which are resistant to in vivo degradation, and which are capable of selectively binding polynucleotides (both DNA and RNA) both extracellularly and intracellularly. Such compounds would be useful in combating diseases by biochemical intervention at the DNA or RNA level.

SUMMARY OF THE INVENTION

Accordingly, it is an object of the invention to provide a class of compounds capable of transport across cellular membranes.

It is another object to provide a class of compounds which are resistant to in vivo degradation.

It is another object to provide a class of compounds capable of selectively and strongly binding a polynucleotide target.

It is another object of this invention to provide a class of compounds capable of selectively and strongly binding a DNA target.

It is another object of this invention to provide a class of compounds capable of selectively and strongly binding a RNA target.

It is another object of this invention to provide a class of compounds capable of selectively and strongly binding a polynucleotide target in vivo.

It as another object of this invention to provide a class of compounds capable of selectively and strongly binding DNA in vivo.

It as another object of this invention to provide a class of compounds capable of selectively and strongly binding RNA in vivo.

It as another object of this invention to provide a class of compounds capable of selectively neutralizing DNA in vivo.

It as another object of this invention to provide a class of compounds capable of selectively neutralizing RNA in vivo.

It as another object of this invention to provide a class of compounds capable of combatting diseases by biochemical intervention at the DNA level.

It is another object of this invention to provide a class of compounds capable of combatting diseases by biochemical intervention at the RNA level.

It is another object of this invention to provide a class of compounds capable of combatting viral diseases.

It is another object of this invention to provide a class of compounds capable of combatting genetically based diseases.

These objects of the invention and others which will become apparent from the description of the invention provided below have now surprisingly been discovered to be satisfied by the inventor's discovery of the following novel class of compounds of formula (I), or a salt thereof:

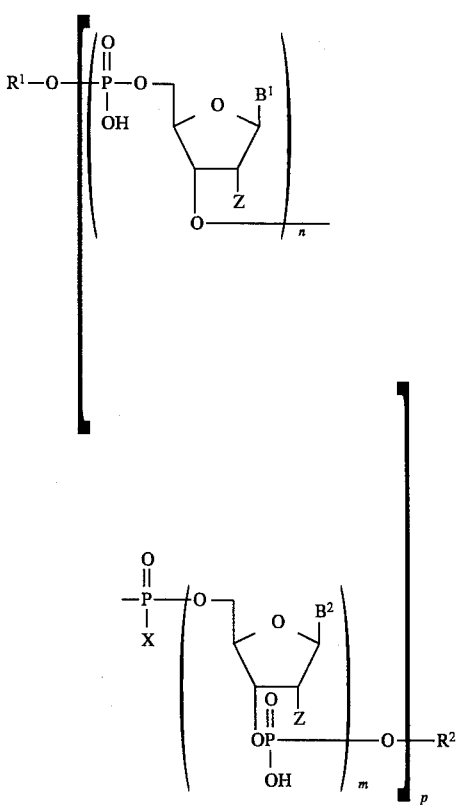

$R^1$ and $R^2$ are each independently H; $C_{1-15}$ saturated or unsaturated acyl; $C_{1-15}$ ether; $C_{1-15}$ acetal; $C_{1-15}$ linear, branched or cyclic, saturated or unsaturated alkyl; phosphate; or sulfate; wherein when said $R^1$ and $R^2$ are a carbon-containing group, said carbon-containing group may be substituted by at least one member selected from the group consisting of halogen atoms (i.e., fluorine, chlorine, bromine or iodine), mercaptan groups containing from 1 to 5 carbon atoms, phosphate groups, sulfate groups, thio groups, dialkyl sulfites wherein each alkyl group contain independently 1 to 5 carbon atoms, amino groups, nitro groups, carboxyl groups and heterocyclic substituents, i.e., 4 to 16-membered cyclic or bicyclic compounds containing at least one nitrogen, oxygen and/or sulfur atom(s). Any $R^1$ or $R^2$ which is a carbon-containing group can also be substituted by a $C_{1-6}$ alkyl substituent interrupted by one carbonyl functionality, or a $C_{1-6}$ alkyl substituent terminated by an aldehyde group or any group $R^1$ and $R^2$ can itself be terminated by an aldehyde group.

$R^1$ and $R^2$ can also be each, independently, substituents which facilitate or control DNA or RNA binding by "classical" mechanisms. Thus $R^1$ and $R^2$ can be a polyamine or a polypyrrole (see, for example, Goodfall et al., *J. Med. Chem.*, vol. 29, pp. 727–733 (1986); Aguley, *Molec. and Cell. Biochem.*, vol. 43, pp. 167–181 (1982); or Feigon, *J. Med. Chem.*, vol. 27, pp. 450–465 (1984)) or an intercalator (see, for example, G. Dougherty and J. R. Tilbrow, *Int'l J. of Biochem.*, vol. 16, p. 1179 (1984)) as defined in the references noted which are hereby incorporated by reference.

$B^1$ and $B^2$ are, independently of any other group $B^1$ or $B^2$ in said compound, a purine or pyrimidine such as an adenine, uracil, guanine, cytosine or thymine moiety, or any other heterocyclic moiety capable of hydrogen-bonding with DNA or RNA. Examples of such heterocyclic moieties include hypoxanthine, xanthine, 6-thioguanine, purine, 6-thiopurine, pyrimidine, 2-thiouracil, 4-thiouracil and other heterocycles capable of forming Watson-Crick base pairs with normal constituent bases of RNA and DNA, as well as Hoogsteen base pairs and base triplets.

X is, independently of any other group X in said compound, a group $NR^3R^4$ or a group $R^5$.

$R^3$ and $R^4$ are each, independently of any other $R^3$ or $R^4$ in the compound, a hydrogen atom, or a $C_{1-16}$ alkyl group which can be linear, cyclic, branched, saturated or unsaturated. All of these groups $R^3$ and $R^4$ can either be unsubstituted or substituted by at least one member selected from the group consisting of halogen atoms (i.e., fluorine, chlorine, bromine or iodine, mercaptan groups containing from 1 to 5 carbon atoms, phosphate groups, sulfate groups, thio groups, dialkyl sulfites wherein each alkyl group contains independently 1 to 5 carbon atoms, amino groups, nitro groups, carboxyl groups and heterocyclic substituents, i.e. 4 to 16-membered cyclic or bicyclic compounds containing at least one nitrogen, oxygen and/or sulfur atom(s). These groups $R^3$ and $R^4$ can also be substituted by at least one $C_{1-6}$ alkyl group interrupted by a carbonyl functionality or they can be substituted by at least one $C_{1-6}$ alkyl group terminated by an aldehyde functionality, or any group $R^3$ and $R^4$ can also be terminated by an aldehyde group. Examples of $R^3$ and $R^4$ include octyl, decyl, pentadecyl, 10-cyclopentyldecyl, or derivatives of these containing phenyl, thiophene, pyrrole, furan, aldehyde, keto, thio, amino or imino groups or double bonds.

$R^3$ and $R^4$ can also be each, independently of any other $R^3$ or $R^4$ in said compound, H; $C_{1-16}$ linear, branched or cyclic, saturated or unsaturated alkyl; $C_{1-16}$ linear, branched or cyclic, saturated or unsaturated alkyl containing at least one member selected from the group consisting of halogens, phenyl, thiophene, furan, pyrrole, keto groups, aldehyde groups, thiol groups, amino groups, imino groups, double bonds, triple bonds, an oxygen atom, and a sulfur atom.

$R^3$ and $R^4$ can be each, independently of any other group $R^3$ or $R^4$ in the compound, a $C_{1-16}$ haloalkyl group which can be linear, cyclic, branched, saturated or unsaturated, wherein the halogen atoms of the haloalkyl substituent are fluorine, chlorine, bromine or iodine, for example, mono-, di- and trichlorodecyl, mono-, di- and tribromodecyl, and mono- or di-triiododecyl, a $C_{1-16}$ ether or a $C_{1-16}$ thioether.

Also included within the scope of this invention are groups $NR^3R^4$ in which $R^3$ or $R^4$ each independently contain appended substituents, for example polyamines, intercalators, groove binders, that can further augment or control polynucleotide binding by the probe molecule.

$R^5$ is, independently of any other group $R^5$ in the molecule, a $C_{2-20}$ alkyl group which can be linear, cyclic, branched, saturated or unsaturated. Any one of these groups $R^5$ can be substituted by at least one member selected from the group consisting of halogen atoms (i.e. fluorine, chlorine, bromine or iodine), mercaptan groups containing from 1 to 5 carbon atoms, phosphate groups, sulfate groups, thio groups, dialkyl sulfites wherein each alkyl group contains independently 1 to 5 carbon atoms, amino groups, nitro groups, carboxyl groups, and heterocyclic substituents, i.e. 4 to 16-membered cyclic or bicyclic compounds containing at least one nitrogen, oxygen and/or sulfur atom(s). Any of these groups $R^5$ can further be substituted by a $C_{1-6}$ alkyl substituent interrupted by one carbonyl functionality or they can be substituted by $C_{1-6}$ alkyl substituent terminated by an aldehyde functionality, or any one of these groups $R^5$ can be terminated by an aldehyde functionality. In addition, $R^5$ can be any group in accordance with the definitions of $R^3$ and $R^4$ given in this document.

X can also be, independently of any other group X, —O—($C_{2-16}$ alkyl) or —S—($C_{2-16}$ alkyl). Examples of the substituents include N-octylthio, N-butyloxy, 5-cis-octenylthio, 10-phenyldecyloxy, etc.

The compounds of this invention are as defined above with the proviso that (1) only one group $R^3$ or $R^4$ can be hydrogen on any one group $NR^3R^4$ in the molecule, and (2) if the compound is by itself and if one variable X is a group selected from the group consisting of —$OCH_2CCl_3$, —$OC(CH_3)_2CCl_3$, —$NHCH_2CH_2NH_2$, —$NH_2$, and —$OCH_2CCl_3$, then the compound possesses at least two different groups X. In pharmaceutical composition and in the use of the compound of this invention proviso (2) does not apply.

Z is, independently of any other Z in the molecule, H, OH or SH.

n, m and p are each independently an integer of from 1 to 20.

The sum of n, m and p≦20.

BRIEF DESCRIPTION OF THE FIGURES

A more complete appreciation of the invention and many of its advantages will be obtained as the same becomes better understood by reference to the following detailed description when considered in connection with the accompanying figures.

DETAILED DESCRIPTION OF THE PREFERRED EMBODIMENTS

Figure 1:
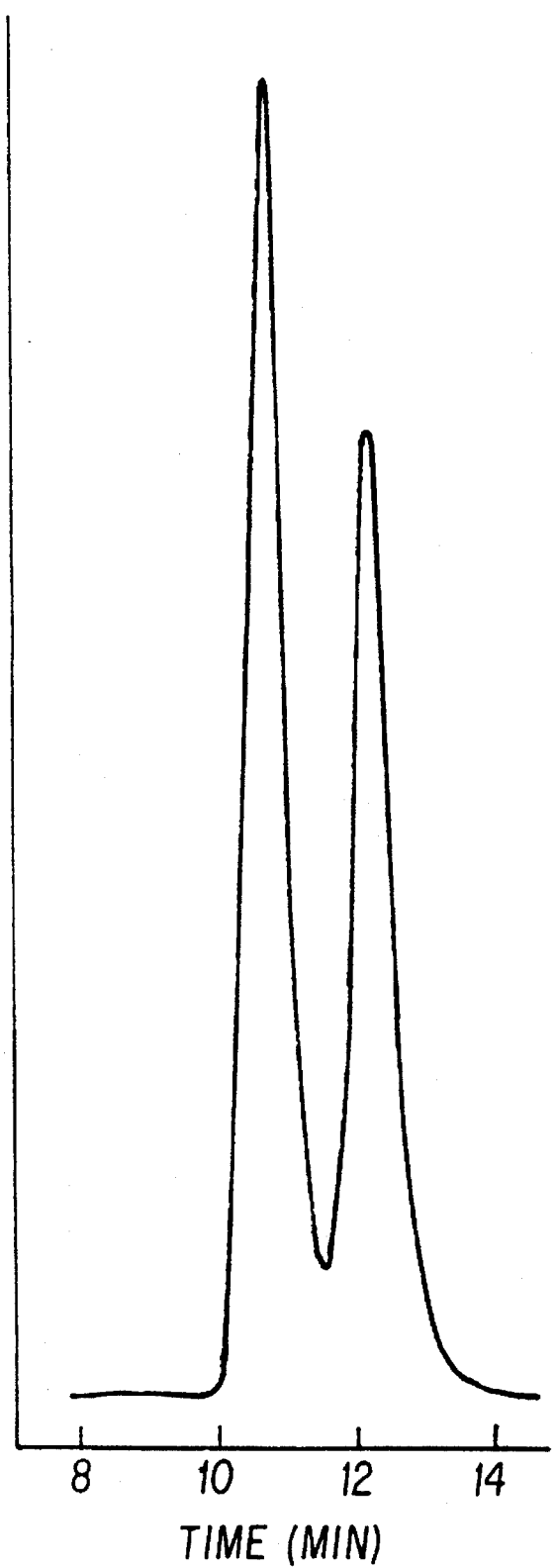
FIG. 1 illustrates the separation of diastereomeric dinucleoside n-octylphosphoramidates 19a. The mixture of diastereomers was applied to a 25×4.6 cm Alltech $C_{18}$ column (10μ) and washed with 35% $CH_3CN$ in 0.1N ammonium formate at a flow rate of 1.0 mL/min. The column was monitored at 254 nm.

The oligonucleotides N-alkylphosphoramidates of the present invention are compounds having the structure or formula (I) provided above. In this formula, Z is H, OH or SH. When Z=OH, one gets (1) more stable duplexes, (2) an altered sugar pucker/conformation, (3) a general base to facilitate certain reactions leading to polynucleotide strand scission, and (4) a group onto which other chemical groups, e.g., nucleic acid cleavers, binding adjuvants, can be appended. However, when Z=OH one also gets diminished chemical and enzymatic stability.

The groups Z in the molecule can either be all the same, or they can each be independently selected from the group of H, OH and SH. When the compound possesses one or more groups Z=OH and the remaining variables Z are H, one obtains probes which possess the following advantages: (1) inclusion of structural adjuvants that can bind or degrade target RNA or DNA is facilitated; and (2) turnover of the probe, enhancing its pharmacokinetic behavior, is also facilitated.

Variables n, m and p are each, independently of any other variable n, m or p in the compound, an integer of from 1 to 20, with the proviso that the sum of variables n, m and p does not exceed 20.

Shorter probes, probes in which the sum of n, m and p falls in the range of 8 to 12 can be used in most cases where the target is single-stranded and biochemically accessible, binding selectivity is not absolutely critical, and target destruction will suffice therapeutically. These types of probes can be used, for example, in antiviral therapy.

Larger probes, probes in which the sum of variables n, m and p is 12 or greater, are required to dissect events within the human genome due to access/selectivity problems.

The compounds of the present invention can be designed to complex to specific segments of either DNA or RNA. In one embodiment of this invention, the compounds of the present invention can be designed to selectively bind to DNA by choosing variables $B^1$ and $B^2$ from adenine, thymine (uracil), guanine, and cytosine.

It should be recognized that the present invention describes a generic, sequence-neutral form of DNA or RNA affinity and that other binding adjuvants can also be included within the structures of the probe molecules to enhance affinity. Of special interest are binding adjuvants, such as intercalators (e.g., ethidium, methidium, proflavine), groove binders (distamycin, netropsin, pyrrolobenzodiazepines) and electrostatic binders (spermine, spermidine, agmatine) and probes containing modified heterocycles (e.g. xanthine, 6-thioguanine, purine) that have special H-binding properties and permit modulation of probe-target interaction.

The oligonucleotides provided by the present invention will associate with their target via Watson-Crick, Hoogsteen or base-triple interaction, and that the binding adjuvants (in the form of N-alkyl substituents, as defined herein) will increase this intrinsic source of affinity. The binding per se renders the target oligonucleotide biochemically dysfunctional, or "tags" the target for destruction by cellular nucleases (e.g. ribonuclease H).

Variable X in formula (I) is a group $NR^3R^4$ or a group $R^5$. When any of these groups is an alkyl group, this definition is intended to include simple hydrocarbon groups which may be linear, cyclic, branched, saturated or unsaturated. These groups may also be halogenated with at least one chlorine, bromine, or iodine atom, or this group containing from 1 to 16 carbon atoms may be interrupted by oxygen atoms or sulphur atoms or a combination of these.

When either group $R^3$ or $R^4$ or $R^5$ is an unsaturated hydrocarbon, these unsaturated hydrocarbons include alkenes and alkynes. The alkenes are preferably cis-alkenes, although both trans-alkenes and mixed cis-/trans-alkenes can also be used.

In a preferred embodiment of this invention, the compound contains no more than three phosphoramidate groups in a single probe molecule, and all of these phosphoramidate groups can be either the same or different. The phosphoramidate structures are evenly spaced within the molecule, or they can be situated at the middle of the molecule and on one end thereof.

The compounds of the invention can be administered via any administration route known. For example, they can be administered intravenously or intramuscularly in solution. They can be administered intranasally as aerosols or drops, and they can be administered with carriers, for example liposomes or nanoparticles or as suppositories. These compounds are administered to a patient in amounts of up to 50 mg per administration until the therapeutic end point is reached.

The probes of the present invention can be used to target messenger RNA of various agents causing diseases. These agents can be infective agents of a bacterial, vital or protozoal nature. Viral agents include AIDS, influenza or herpes. Protozoan agents include, e.g., trypanosomes or malaria.

The compounds provided by the present invention can also be used to target genetic diseases. They can be used to target DNA responsible for these genetic diseases or control regions of DNA, or RNA to block/regulate gene expression.

The compounds of the present invention can be present in their free form or as any of well known physiologically acceptable salt. These salts include mono- and divalent cations commonly used therapeutically, e.g., sodium, potassium, calcium, lithium and magnesium salts, and alkylamine salts, such as polyamine salts.

The oligonucleotide alkylphosphoramidates of this invention can be made by automated solid phase synthesis. For each of these oligonucleotides, it is generally possible to separate the diastereomeric species by reverse phase hplc. Individual isomers bind to their complementary polynucleotides, but with somewhat different affinities.

The nucleoside N-alkylphosphoramidates can be prepared by a few different procedures, but preferably by utilizing the observations of Nemer and Ogilvie (1980), who demonstrated that oxidation of an intermediate dinucleoside trichloroethyl phosphite with iodine in the presence of an alkylamine establishes the requisite N-alkylphosphoramidate linkage. As illustrated in Scheme III, when protected dinucleoside O-methylphosphites were treated with alkylamines, the desired (protected) dinucleoside N-alkylphosphoramidate derivatives were obtained in moderate to good yields, and could be deprotected readily to afford the desired dinucleoside N-phosphoramidates.

Oligonucleotide N-alkylphosphoramidates are also accessible by solid phase synthesis. This is achieved by modification of the method of Matteucci and Caruthers (1981), which involved substitution of $I_2$-alkylamine for $I_2$-$H_2O$ in the oxidative step of the coupling cycle(s) in which the N-alkylphosphoramidate linkage was to be introduced.

Other features of the invention will become apparent in the course of the following descriptions of exemplary embodiments which are given for illustration of the invention and are not intended to be limiting thereof. In the discussion below the inventor provides plausible theoretical explanations of how his novel compound might be understood to work. These explanations are not provided to limit this invention in any manner, but are simply provided for the benefit of the reader.

In the examples section provided below, the inventor discusses a few different methods for the preparation of oligonucleotide N-alkylphosphoramidates which were compared directly. One of these, which involves the use of protected nucleoside phosphites as building blocks, provided the requisite N-alkylphosphoramidates via oxidation of the intermediate dinucleoside methyl phosphites with iodine in the presence of the appropriate alkylamine.

This method was found to have several attractive features, including the use of building blocks identical with those employed for the synthesis of DNA, and compatibility with procedures and instruments employed for the stepwise synthesis of oligonucleotides by solution and solid phase methods. This procedure was used to make several di-, tri- and tetranucleotide N-alkylphosphoramidates derived from deoxyadenosine and thymidine; alkyl substituents included N,N-dimethyl, N-butyl, N-octyl, N-dodecyl and N-(5-aminopentyl). The aminoalkyl derivative of TpT (24) was used to demonstrate the feasibility of introducing an intercalative agent to the alkylphosphoramidate moiety of such derivatives.

The oligonucleotide N-alkylphosphoramidates were separated into their component diastereomers and characterized structurally by a number of techniques including circular dichroism, high field $^1$H-NMR spectroscopy, FAB mass spectrometry and enzymatic digestion to authentic nucleosides and nucleotides. Physicochemical characterization of several di- and trinucleotide alkylphosphoramidates revealed that the adenine nucleotide analogs formed stable complexes with poly(thymidylic acid).

The stabilities of these complexes were found to increase with increasing chain length of the N-alkylphosphoramidate substituents. The N-alkylphosphoramidate substituents enhance the binding of certain oligonucleotides to their complementary polynucleotides, providing a novel source of polynucleotide affinity.

This invention is due in part to the discovery of a polynucleotide binding adjuvant that works by a novel principle. The inventor has found that in addition to the known types of DNA binders (intercalators, groove binders, polycations), there are a number of highly lipophilic natural products that associate with DNA or RNA in a sequence-neutral fashion and with good affinity.

Presumably, the source of the affinity derives from the fact that the interior of the DNA or RNA duplex is the most lipophilic component of an aqueous solution containing dissolved DNA or RNA. Admixture of a lipophilic molecule to this aqueous DNA solution would then result in association of the lipophilic probe with the most lipophilic portion of the DNA.

This principle was then extended to the preparation of dinucleotides of type II, i.e., analogs of the Letsinger-Schott dinucleotide 1.

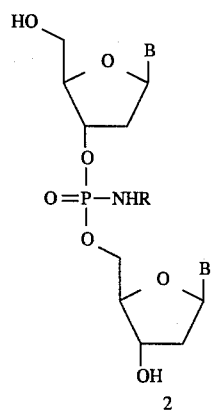

2

-continued where B = adenine or thymine, and R = $C_4H_9$, $C_8H_{17}$ or $C_{12}H_{25}$.

When the adenine dinucleotides of type 2 were studied as binders of poly T, interesting results were obtained. As shown in Table 1, the presence of

TABLE I

Binding of Poly T to

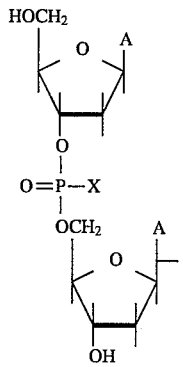

| X | Tm | % Hypochromicity |
|---|---|---|
| 0- | 7–9 | 30–36 |
| $NH(CH_2)_3CH_3$ | 17, 12[a] | 48, 42[a] |
| $NH(CH_2)_{11}CH_3$ | 20[a] | 30[a] |

[a] in the presence of 15% MeOH the alkyl groups resulted in an increase in the Tm (i.e., melting temperature) values. The extent of increase in Tm was also proportional to the length of the alkyl substituent. The observation of an increase in Tm has also been made for oligonucleotide phosphoramidates containing intercalators rather than as alkyl group (Letsinger and Schott, 1981; Asseline et al., 1984; Helene et al., 1985). This evidences that the lipophilic alkylphosphoramidate groups of the present invention promoted the binding of these oligonucleotides to poly T.

The hypochromicity values are also shown in Table I for some of the dinucleotides studied. Unlike the results typically obtained with intercalators, where increased affinity correlates with increased base stacking (and hence with the increased hypochromicity), dinucleotides 2 exhibited an optimum for % hypochromicity. This may reflect a disordering of the formed duplex by the lipophilic alkyl chain as the latter extends beyond a certain size.

Aside from their ability to stablize a duplex with their Watson-Crick complementary sequences, the nucleotide phosphoramidates provided by this invention were found to have the following two additional important features. They are surprising lipophilic, making them capable of transport across cellular membranes and they are refractory to nucleolytic degradation at the phosphoramidate linkages.

The preparation of oligonucleotides containing modified phosphodiester linkages is of current interest as a source of sequence-specific nucleic acid probes (Miller et al., 1981; Letsinger & Schott, 1981; Asseline et al., 1984; Chu & Orgel, 1985; Dreyer & Dervan, 1985; Thuong et al., 1987). Nucleoside phosphoramites have been prepared previously by several procedures involving both tri- and pentavalent phosphorous intermediates. These have included the condensation of nucleoside phosphate diesters with amines in the presence of triphenylphosphine-$CCl_4$ (Appel, 1975; Stec, 1983), nucleophilic substitution of nucleoside phosphate triesters with alkylamines (Meyer et al., 1973; Juodka & Smrt, 1974; Letsinger et al., 1986), addition of alkyl and aryl azides to phosphites (Cramer et al., 1972; Letsinger & Schott, 1981), as well as the oxidation of intermediate nucleoside phosphites (Nemer & Ogilvie, 1980 a,b) or nucleoside H-phosphonate diesters (Froehler, 1986) with iodine in the presence of alkylamines.

Experiments are described below which illustrate such transformations for the preparation of oligonucleotide phosphoramides, both by solution and solid phase techniques. Also described is chromatographic resolution and analysis of the formed diastereomers, and their analysis by spectral and degradative techniques.

The association of a series of diadenosine N-alkylphosphoramidates with poly(thymidylic acid) was characterized by measurement of Tm and hypochromicity values, as well as by determination of the stoichiometry of association. These measurements indicated that the N-alkyl groups promoted the binding of the diadenosine N-alkylphosphoramidate derivatives to poly T, and the affinity increased with increasing alkyl chain length. The implications of this novel source of affinity for the design of sequence-specific nucleic acid probes is discussed.

Because there has been no direct comparison of the several methods available for the preparation of oligodeoxynucleoside N-alkylphosphoramidates, the study was initiated by comparison of a few promising methods.

The condensation of nucleoside phosphate diesters with amines in the presence of triphenylphosphine-$CCl_4$ (Appel, 1975) has been used previously for the preparation of nucleoside phosphoranilidate derivatives (Stec, 1983) with the desired products being obtained in moderate yield. Application of this method for the synthesis of deoxynucleoside N-alkylphosphoramidates was attempted using fully protected thymidylyl(3'→5')-thymidine derivative 2 (Scheme I).

Scheme I:

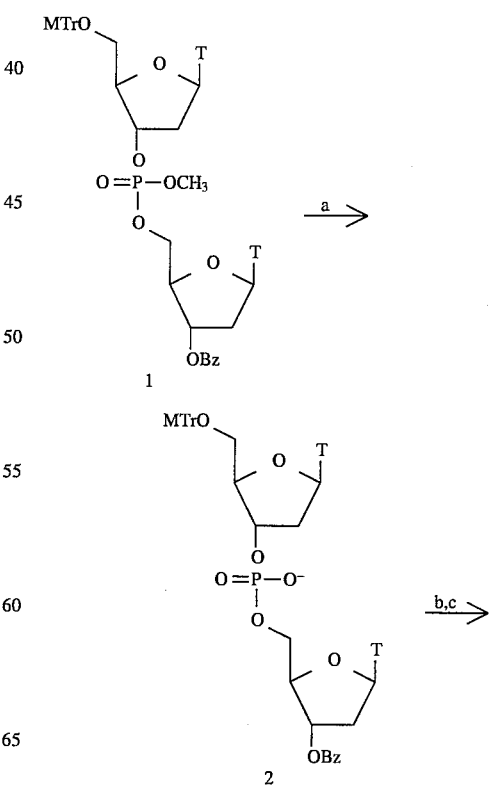

Scheme I: -continued

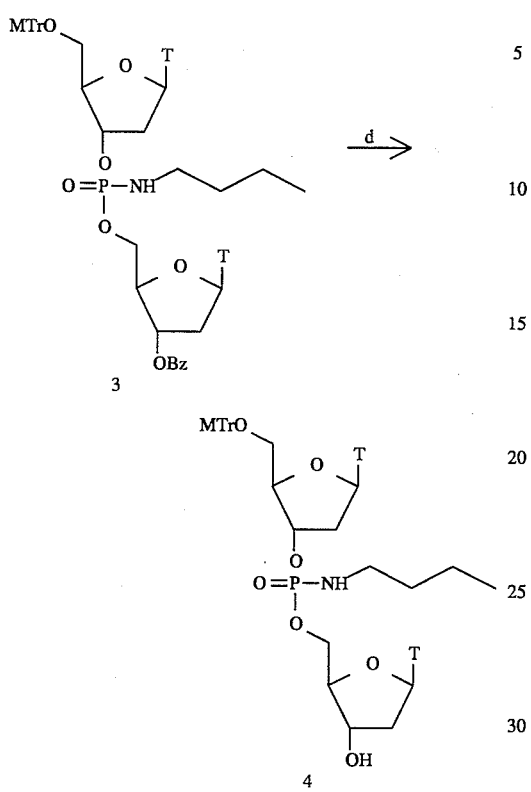

Reagents: (a) C$_6$H$_5$SH, Et$_3$N, dioxane;
(b) (C$_6$H$_5$)$_3$P, CCl$_4$;
(c) n-C$_4$H$_9$NH$_2$;
(d) t-C$_4$H$_9$NH$_2$, CH$_3$OH.

Successive treatments of 2 with ~3 equivalents of triphenylphosphine-CCl$_4$ in CH$_3$CN-pyridine, and then with an excess of n-butylamine, afforded dinucleoside n-butylphosphoramidate 3 in 24% isolated yield. The structures of 3, and its debenzoylated derivative 4, were consistent with the behavior of each on silica gel TLC, and with their measured UV and high field $^1$H-NMR spectra (Table II).

TABLE (II)

Preparation of Dinucleoside N-Alkylphosphoramidates 17 and 19[a]

| Compound | Base | R | R' | Yield (%) | R$_f$ Value[b] |
|---|---|---|---|---|---|
| 3 | T | MTr | n-C$_4$H$_9$ | 48 | |
| 17a | T | MTr | n-C$_8$H$_{17}$ | 76 | |
| 17b | T | MTr | n-C$_{12}$H$_{25}$ | 56 | |
| 17c | A$^{Bz}$ | DMTr | n-C$_4$H$_9$ | 54 | |
| 17d | A$^{Bz}$ | DMTr | n-C$_8$H$_{17}$ | 83 | |
| 17e | A$^{Bz}$ | DMTr | n-C$_{12}$H$_{25}$ | 79 | |
| 17f | A$^{Bz}$ | DMTr | (CH$_3$)$_2$[c] | 87 | |
| 19g | T | H | n-C$_4$H$_9$ | 58 | 0.45 |
| 19a | T | H | n-C$_8$H$_{17}$ | 77 | 0.60 |
| 19b | T | H | n-C$_{12}$H$_{25}$ | 100 | 0.66 |
| 19c | A | H | n-C$_4$H$_9$ | 81 | 0.26 |
| 19d | A | H | n-C$_8$H$_{17}$ | 59 | 0.38 |
| 19e | A | H | n-C$_{12}$H$_{25}$ | 77 | 0.50 |
| 19f | A | H | (CH$_3$)$_2$[c] | 94 | 0.26 |

TABLE (II)-continued

Preparation of Dinucleoside N-Alkylphosphoramidates 17 and 19[a]

| Compound | Base | R | R' | Yield (%) | R$_f$ Value[b] |
|---|---|---|---|---|---|

[a]See Experimental Procedures for methods of preparation.
[b]Silica gel TLC, development with 5:1 CH$_2$Cl$_2$—CH$_3$OH.
[c]N,N-Dimethylphosphoramidate derivative.

Dinucleoside n-butylphosphoramidate 4 was also synthesized on a polymeric support by modification of the method of Matteucci and Caruthers (1981) (Scheme II).

Scheme II:

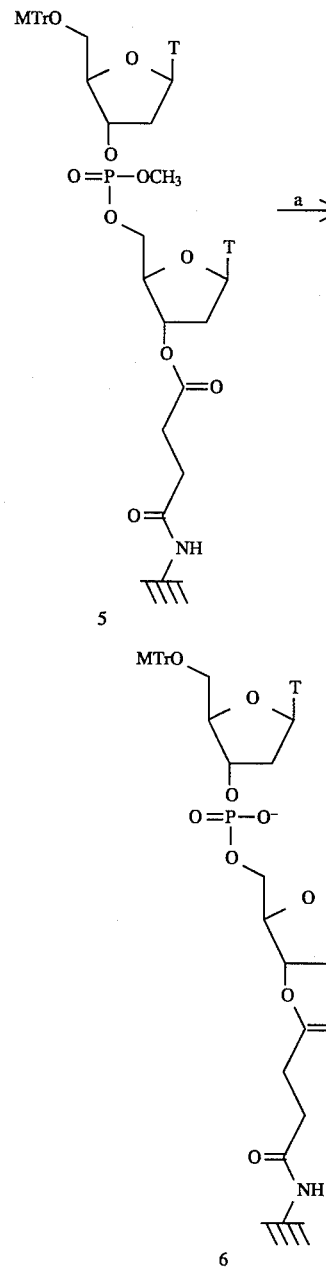

-continued
Scheme II:

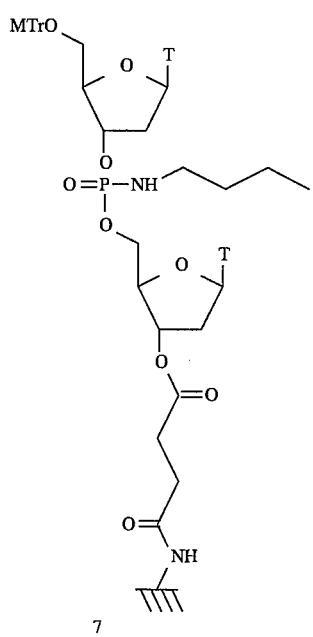

Reagents: (a) C₆H₅SH, Et₃N, dioxane;
(b) (C₆H₅)₃P, CCl₄;
(c) n-C₄H₉NH₂;
(d) t-C₄H₉NH₂, CH₃OH.

Compound 4 was obtained in ~70% overall yield from the resin-bound precursor 5, and was shown to be identical in all respects with the product obtained by solution phase synthesis.

The preparation of nucleoside N-alkylphosphoramidates via treatment of nucleoside phenylphosphite derivatives 8 with n-hexylazide (25° C., 4 days) was also studied (Scheme III).

Scheme III.

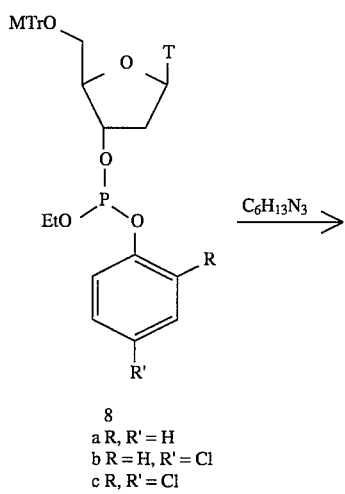

8
a R, R' = H
b R = H, R' = Cl
c R, R' = Cl

-continued
Scheme III.

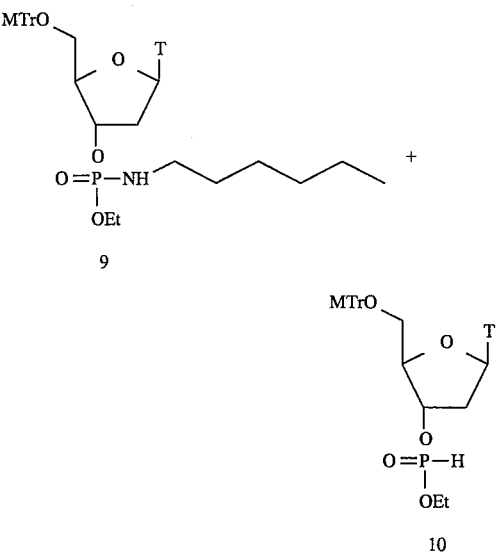

The use of 8a and 8b, containing phenyl and 4-chlorophenyl phosphites, respectively, led only to solvolysis and other decomposition products. On the other hand, nucleoside 8c provided the desired nucleoside n-hexylphosphoramide derivative 9 in 54% yield, along with quantities of nucleoside H-phosphonate 10 and 5'-O-(methoxytrityl)thymidine.

For comparative purposes, the reaction of 8c with methyl azidoacetate, a transformation more closely analogous to that reported by Letsinger & Schott (1981) was also studied (Scheme IV).

Scheme IV.

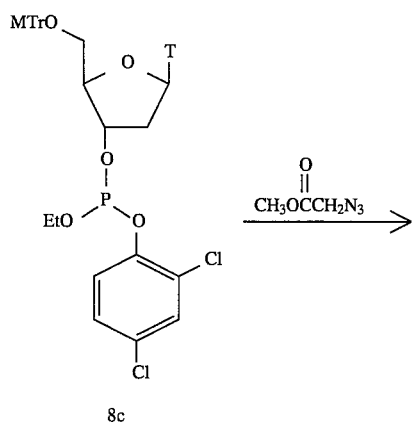

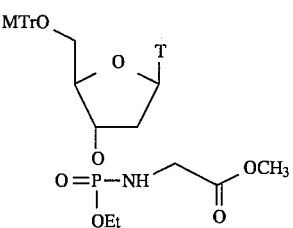

Not surprisingly this reaction proceeded with greater facility, providing compound 11 in 68% isolated yield after 2 days at 25° C.

The procedure reported by Nemer and Ogilvie (1980), involving oxidation of an intermediate dinucleoside trichloroethyl phosphite with iodine in the presence of an alkylamine, appeared particularly attractive as the oxidation was rapid and essentially quantitative, and the reported conditions appeared amenable for adaptation to solid phase synthesis. Because the formation of an N-alkylphosphoramidates by this procedure must involve the loss of one of the original phosphite substituents, it was first sought to determine the extent to which this step might proceed selectively. Accordingly, deoxynucleoside 3'-phosphite 12 was prepared and treated with a slight excess of $I_2$ in dry tetrahydrofuran-n-butylamine. Work-up of the reaction mixture provided ethyl 5'-0-(dimethoxytrityl)thymidine 3'-(N-n-butyl)phosphoramidate (13) in 45% isolated yield; very little (<10%) of the putative O-methyl analog 14 could be detected (Scheme V).

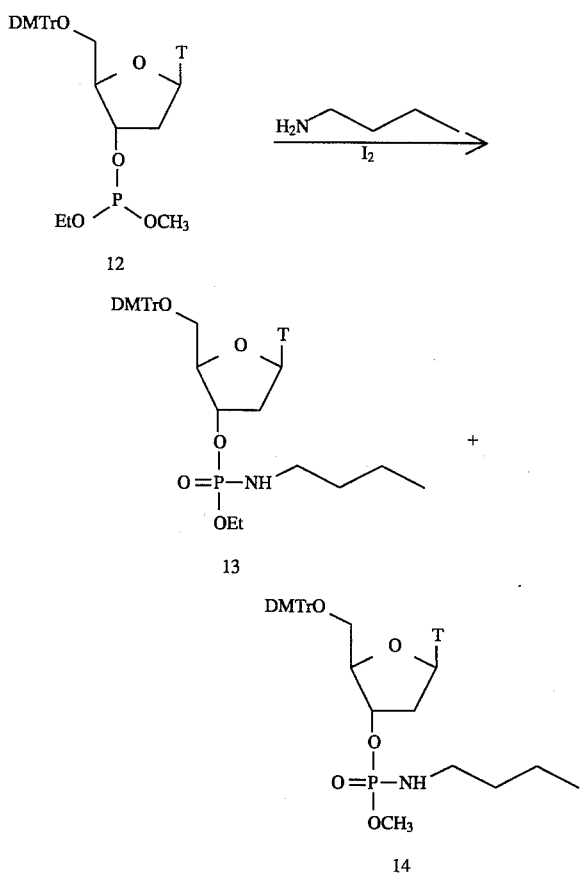

Scheme V.

The selective loss of the methyl substituent suggested that this approach might well afford the requisite oligonucleotide N-alkylphosphoramidates. Further, as O-methyl protection is frequently employed for phosphate esters during solid phase oligonucleotide synthesis (Matteucci & Caruthers, 1981), the protected nucleoside 3'-(O-methyl), N,N-diisopropylamino)phosphoramidites employed as building blocks in such schemes could potentially be employed as precursors both for phosphate ester and phosphoramidate linkages.

As outlined in Scheme (VI), two different dinucleoside O-methyl phosphites were prepared and each was treated with a few different alkylamines in the presence of $I_2$.

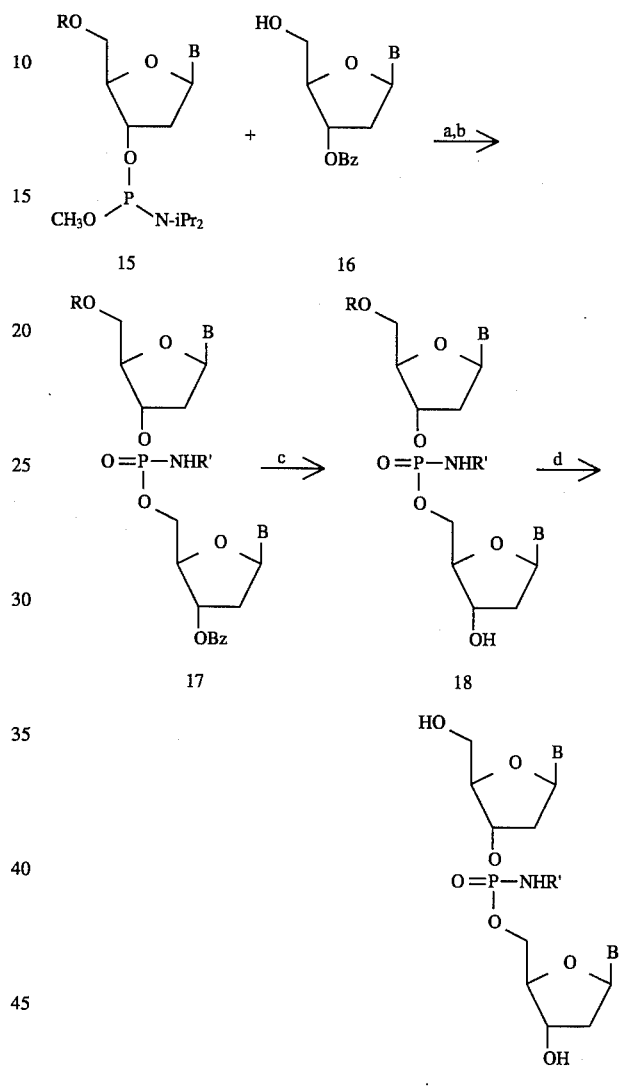

Scheme (VI):

Reagents: (a) tetrazole, $CH_3CN$;
(b) $I_2$, $R'NH_2 THF$;
(c) $t-C_4H_9NH_2$, $CH_3OH$, 45° C.;
(d) aq HOAc.

The resulting fully protected dinucleoside N-alkylphosphoramidates (3, 17a–17f) were purified by chromatography on silica gel; the yields of each (48–87%) are given in Table II. Successive debenzoylation (t-BuNH$_2$, CH$_3$OH) and detritylation (80% aq CH$_3$COOH) afforded the respective dinucleoside N-alkylphosphoramidates 19a–19g in isolated yields of 58–100%, as shown in Table II supra.

Products were characterized by silica gel TLC and reverse phase HPLC, as well as by UV and 360 MHz $^1$H-NMR spectroscopy (see Table III and Table IV, infra).

TABLE III

360 Mz ¹H-NMR Spectra of Dinucleoside Alkylphosphoramidate Derivatives 17[a]

| Proton | Chemical Shift Values (δ) | | | | | | |
|---|---|---|---|---|---|---|---|
| | 3 | 17a | 17b | 17c | 17d | 17e | 17f |
| H-6 | 7.54 | 7.53 | 7.58 | | | | |
| H-2 | | | | 8.80,8.73 | 8.82,8.73 | 8.82,8.73 | 8.33,8.30 |
| | | | | 8.65,8.43 | 8.67,8.63 | 8.66,8.62 | 8.27,8.23 |
| H-8 | | | | 8.48,8.33 | 8.50,8.37 | 8.49,8.35 | 8.06,7.97 |
| | | | | 8.18,8.13 | 8.19,8.13 | 8.18,8.12 | 7.95,7.94 |
| 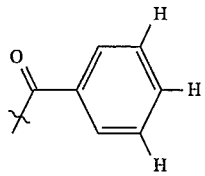 | 8.1–8.0 | 8.0 | 8.0 | 8.0 | 8.0 | 8.0 | 8.0–7.8 |
| Aromatic H | 7.6–7.2 | 7.6–7.2 | 7.4–7.2 | 7.6–7.2 | 7.6–7.2 | 7.6–7.2 | 7.4–7.2 |
| 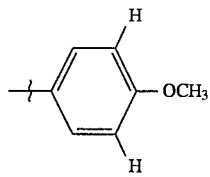 | 6.9–6.8 | 6.9–6.8 | 6.85 | 6.8 | 6.8 | 6.8 | 6.8 |
| H-1' | 6.5–6.3 | 6.5–6.3 | 6.4,6.2 | 6.6,6.5 | 6.6,6.5 | 6.6 | 6.48,6.41 |
| H-3' | 5.56,5.47,5.15 | 5.56,5.47,5.15 | 5.1 | 5.8,5.25,5.2 | 5.8,5.25,5.2 | 5.8,5.2 | 5.92,5.82,5.1 |
| H-4', H-5'(pN) | 4.4–4.2 | 4.4–4.2 | 4.6–4.0 | 4.5–4.3 | 4.5–4.3 | 4.5–4.3 | 4.8–4.0 |
| $OCH_3$ | 3.80,3.78 | 3.79,3.77 | 3.80 | 3.77,3.75,3.74 | 3.77,3.75,3.74 | 3.77,3.75,3.74 | 3.78 |
| H-5' (Np) | 3.5–3.3 | 3.6–3.3 | 3.6–3.3 | 3.4 | 3.4 | 3.4 | 3.4 |
| NH$CH_2$, H-2' | 3.0–2.3 | 3.0–2.2 | 3.2–2.1 | 3.1–2.8 | 3.2–2.8 | 3.1–2.8 | 3.0–2.5 |
| $CH_3$ (T) | 1.93,1.91 | 1.94,1.92 | 1.88 | | | | |
| $-(CH_2)_n-$ | 1.5–1.2 | 1.5–1.2 | 1.6–1.1 | 1.4–1.2 | 1.3–1.1 | 1.4–1.1 | |
| $CH_3$ | 1.0–0.8 | 0.87 | 0.87 | 1.0–0.8 | 0.9–0.8 | 0.9 | 2.66,2.62 |

[a]Recorded in $CDCl_3$ using $(CH_3)_4Si$ as an internal standard.

TABLE IV

360 MHz ¹H-NMR Spectra of Dinucleoside Alkylphosphoramidate Derivatives 19[a]

| Proton | Chemical Shift Values (δ) | | | | | | |
|---|---|---|---|---|---|---|---|
| | 19g | 19a | 19b | 19c | 19d | 19e | 19f[b] |
| H-6 | 7.56,7.23 | 7.68,7.41,7.32 | 7.73,7.44,7.37 | | | | |
| H-2 | | | | 8.01,8.00 | 8.02,8.00 | 8.18,8.17 | 8.18,8.16 |
| | | | | 7.97 | 7.99,7.97 | 8.14 | 8.14,8.13 |
| H-8 | | | | 7.87,7.85 | 7.88,7.82 | 8.00,7.97 | 8.06,8.02 |
| | | | | 7.82,7.76 | 7.81,7.77 | 7.89,7.85 | 7.88,7.94 |
| H-1' | 6.18–6.13 | 6.3 | 6.3 | 6.2–6.1 | 6.2,6.0 | 6.4–5.9 | 6.33,6.30 |
| H-3'(pN) | 4.86 | 5.08 | 5.05 | 4.9 | 4.9 | 5.1 | 5.04 |
| H-3'(Np) | 4.3–4.2 | 4.45 | 4.4 | 4.4 | 4.4 | 4.5 | 4.5 |
| H-4', H-5' | 4.0–3.6 | 4.2–4.0 | 4.2–4.1 | 4.2–3.4 | 4.2–3.4 | 4.3–3.2 | 4.3–3.7 |
| | | 3.8,3.6 | 4.1,3.8 | | | | |
| NH$CH_2$, H-2' | 2.8–2.7 | 2.9–2.1 | 2.9–2.8 | c | c | c | 3.0–2.4 |
| | 2.4–2.0 | | 2.5–2.0 | | | | |
| $CH_3$(T) | 1.78 | 1.92,1.90 | 1.92,1.88 | | | | |
| $-(CH_2)_n-$ | 1.5–1.4 | 1.5–1.3 | 1.4–1.4 | 1.2–1.0 | 1.2–1.0 | 1.3–1.0 | |
| | 1.35–1.1 | | 1.4–1.1 | | | | |
| $CH_3$ | 0.8–0.7 | 0.87 | 0.90 | 0.7 | 0.6–0.7 | 0.8–0.7 | 2.62,2.59 |

[a]Recorded in $CDCl_3$-DMSO-$d_6$.
[b]Recorded in $CDCl_3$-$CD_3OD$.
[c]Not assigned.

Dinucleoside N-alkylphosphoramidates 19a, 19b and 19g were also characterized by the appearance of the respective molecular ions in their FAB mass spectra (positive and negative ion; glycerol matrix). Each of the tritylated and deprotected dinucleoside N-alkylphosphoramidates (18 and 19, respectively) could be separated by reverse phase HPLC ($CH_3CN$-$H_2O$ mixtures) into two components present in approximately equal amounts (see, e.g., FIG. 1). In each case, the high field ¹H-NMR spectra of the constituents were consistent with their formulation as diastereomers. In some cases the two diastereomers were evaluated separately for their ability to associate with the complementary single stranded nucleic acid (vide infra).

Figure 2:
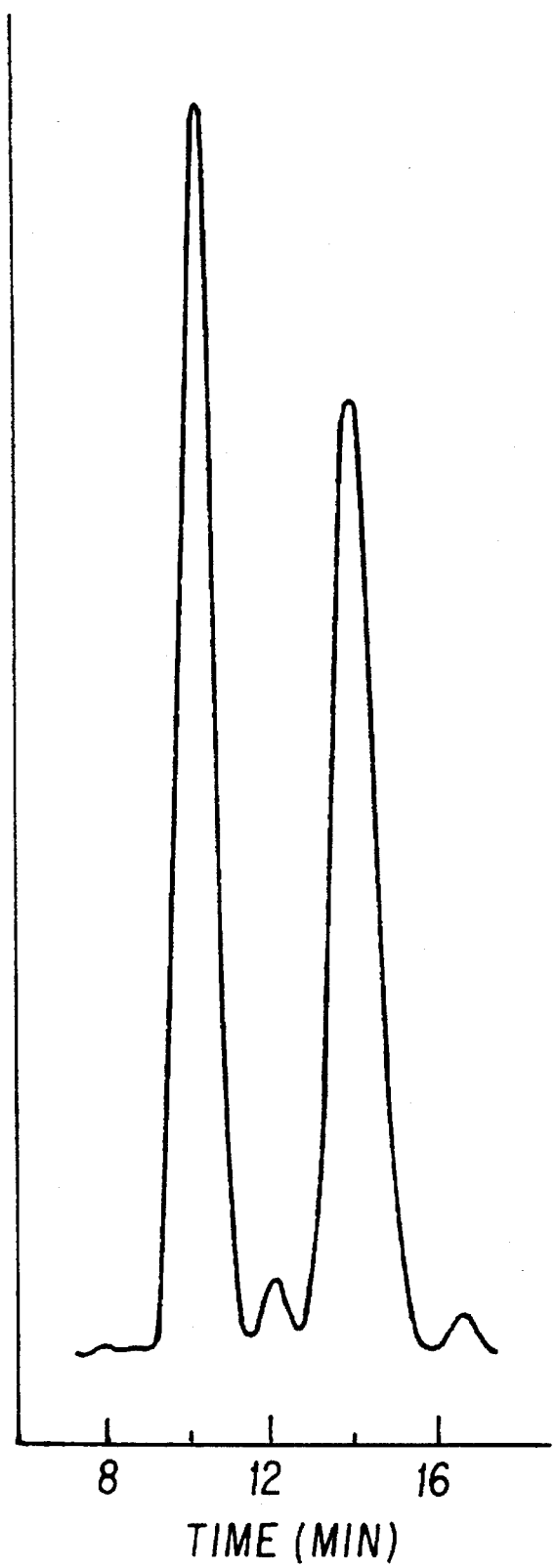
FIG. 2 illustrates the separation of diastereomeric DMTr-22 on reverse phase HPLC. The diastereomeric mixture was separated preparatively on a 25×1.0 cm $C_{18}$ column (10μ) which was washed with 35% $CH_3CN$ in 0.02N triethylammonium acetate, pH 6.9, at a flow rate of 6 mL/min.

To evaluate the applicability of this approach for the elaboration of oligodeoxynucleotide N-alkylphosphoramidates, a few different tetranucleotides were prepared by solid phase synthesis. Each of these contained a single N-alkylphosphoramidate linkage at one of the two terminal positions. Synthesis of the oligonucleotides was carried out by the method of Matteucci and Caruthers (1981), with the exception that introduction of the alkylphosphoramidate linkages were accomplished by substitution of $I_2$-alkylamine treatment for $I_2$-$H_2O$ in the oxidative step of the coupling cycle. Following partial deblocking and removal from the column (t-butylamine-$CH_3OH$), the tritylated tetranucleotides were purified by preparative HPLC on a $C_{18}$ reverse phase column. Elution with 0.02–0.04M tetraethylammonium acetate, pH 6.9, containing an appropriate amount of acetonitrile effected purification of the oligonucleotides and separation of the diastereomers, as illustrated in FIG. 2 for tetranucleotide DMTr-22.

Because the method of solid phase synthesis employed here proceeds from the 3'-end of the nascent oligonucleotide, the successful synthesis of tetranucleotide analog 22 (Scheme VII) demonstrated the stability of the N-alkylphosphoramidate bond during the subsequent condensation, oxidation and detritylation procedures. In addition, during the synthesis of 22 a small amount of the solid support was removed after the first condensation-oxidation cycle and subjected to complete deprotection. This procedure yielded a diastereomeric mixture identical in all respects (¹H-NMR, silica gel TLC, reverse phase HPLC) with 19g prepared by solution phase synthesis.

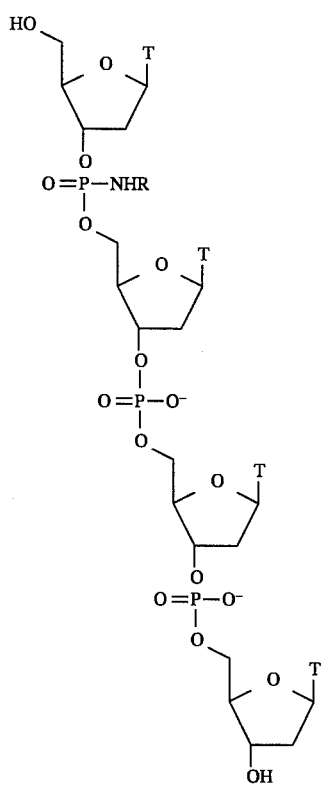

20 R = $C_4H_9$
21 R = $C_{12}H_{25}$

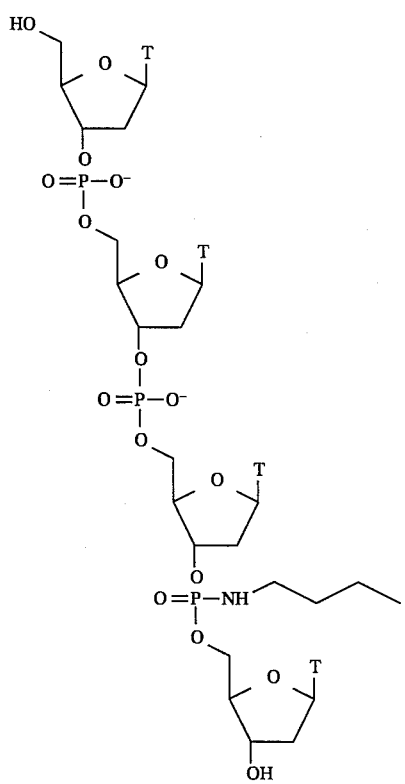

22

Characterization of tetrathymidylate analogs 20 to 22 included enzymatic digestion of each with nuclease P1 and alkaline phosphatase (Connolly et al., 1984). Dinucleoside N-alkylphosphoramidate 19a was shown to be resistant to nuclease P1 under conditions that led to complete hydrolysis of TpT. Treatment of a single diastereomer of 22 with nuclease P1 gave three products, including equal amounts of pT and T. Further treatment with calf intestine alkaline phosphatase coverted the product mixture to a mixture of thymidine and a single diastereomer of 19g. Analogous digestion of 20 and 21 with nuclease P1 resulted in the formation of 19g and 19b, respectively, plus pT. In each case (20 to 22), digestion of the diastereomic mixture of tetranucleotides was found to produce both diastereomers of its respective dinucleoside N-alkylphosphoramidate 19. Each of the diastereomers of the tetranucleotide was shown to lead exclusively to one of the two diastereomers of 19.

In recent years, numerous reports have described the synthesis of oligonucleotides modified to contain adjuvants useful in DNA binding (Letsinger & Schott, 1981; Asseline et al., 1984; Helene et al., 1985; Thuong et al., 1987), site-selective alkylation (Vlassov et al., 1985; Knorre et al., 1985ab; Zarytova et al., 1986; Iverson & Dervan, 1987) or cleavage (Boutorin et al., 1984; Chu & Orgel, 1985; Dreyer & Dervan, 1985; Le Doan et al., 1986; Boidot-Forget et al., 1986, 1987).

The chemistry described here is applicable for the synthesis of such modified oligonucleotides, and it was attempted to prepare a representative dinucleoside phosphoramidate 26. As outlined in Scheme (VIII), key intermediate 24 was prepared by I$_2$-diaminopentane oxidation of the dinucleoside O-methyl phosphite derived from 15+23.

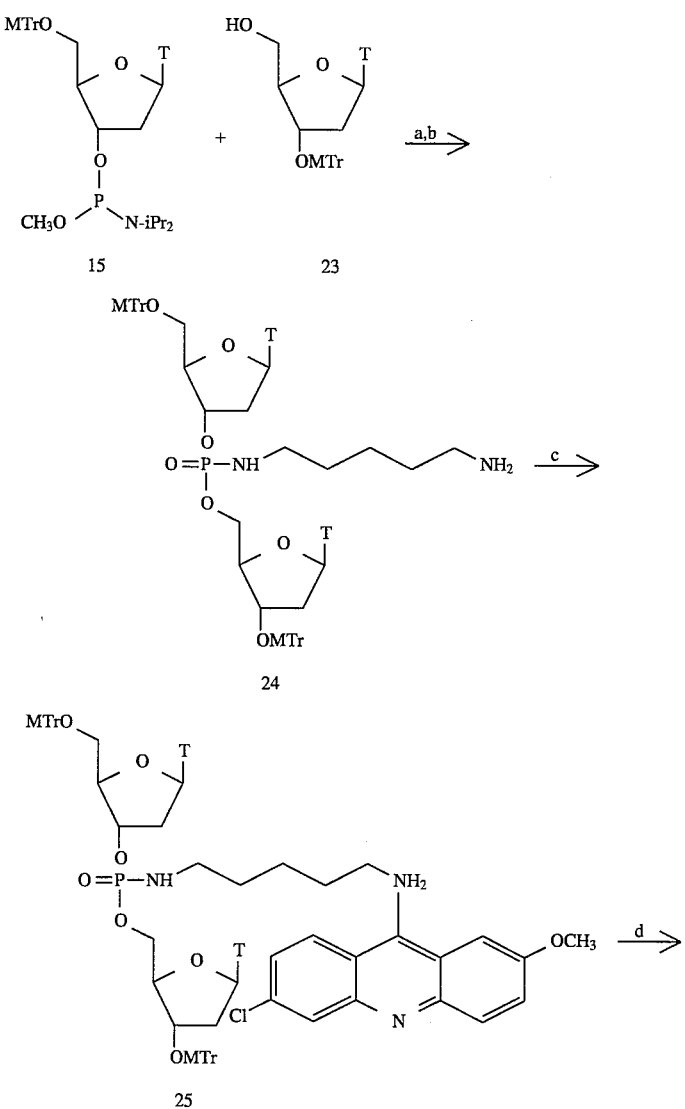

-continued
Scheme (VIII):

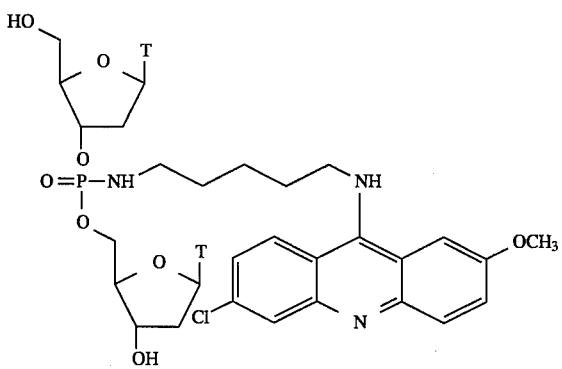

26

Reagents: (a) tetrazole, CH₃CN;
(b) I₂, NH₂(CH₂)₅NH₂; THF;
(c) 6-chloro-9-(p-chlorophenoxy)-2-methoxyacridine;
(d) 2% CF₃COOH in CH₂Cl₂

Individual diastereomers of 24 were obtained by silica gel flash chromatography. Each was treated separately with 6-chloro-9-(p-chlorophenoxy)-2-methoxyacridine at 60° C. overnight to produce 25. Following detritylation (2% CF₃COOH in CH₂Cl₂, 30 min) each of the diastereomers of 26 was isolated by precipitation of its trifluoroacetate salt from a large volume of ether. The less and more polar isomers were obtained in overall yields from 24 of 64% and 54%, respectively. Compound 26 was also prepared by solid phase synthesis in analogy with the synthesis of 20–22.

The ultraviolet hypochromicities and circular dichroism (CD) spectra of the individual oligoadenylate N-alkylphosphoramidates indicated a diminution of base stacking relative to d(ApA) and d(ApApA). The magnitude of the hypochromic effect was not affected by the nature of the N-alkyl group (Table V), in contrast to earlier reports concerning the hypochromicities of alkyl phosphotriesters (Miller et al., 1971; Letsinger et al., 1986).

TABLE (V)

Binding of Adenine Oligonucleotides to Poly(thymidylic acid)[a]

| | Hypochromicity (%) | | Tm(°C.) determined by | |
|---|---|---|---|---|
| Compound | single strand | annealing[b] | Heating[b,c] | Cooling[b,c] |
| d(ApA) | 17[g] | 36 | 9 | 8 |
| | | 30[d] | 7[d] | 5[d] |
| d(ApA) (19f)<br>\|<br>N(CH₃)₂ | 7 | — | — | — |
| d(ApA) (19c)<br>\|<br>NHC₄H₉ | 7 | 48<br>42[d] | 17<br>12[d] | 17<br>10[d] |
| d(ApA) (19d)<br>\|<br>NHC₈H₁₇ | 7 | — | — | — |
| d(ApA) (19e)<br>\|<br>NHC₁₂H₂₅ | 7 | 30[d] | 20[d] | 16[d] |
| 19e - more polar | — | 31[d] | 20[d] | 16[d] |

TABLE (V)-continued

Binding of Adenine Oligonucleotides to Poly(thymidylic acid)[a]

| | Hypochromicity (%) | | Tm(°C.) determined by | |
|---|---|---|---|---|
| Compound | single strand | annealing[b] | Heating[b,c] | Cooling[b,c] |
| diastereomer[e]<br>19e - less polar diastereomer[e] | — | 26[d] | 19[d] | 15[d] |
| d(ApApA) | 27[h] | 36 | 29 (0.1)<br>29 (1.0) | 28 |
| d(ApApA)[f]<br>\|<br>NHC₁₂H₂₅ | 10 | 32 | 40 (1)<br>40 92) | 31 (0.5)<br>31 (1) |

[a]Carried out as described under Experimental Procedures.
[b]All determinations were made in 10 mM Tris-HCl, pH 7.5, containing 10 mM MgCl₂, except where CH₃OH was added in addition.
[c]Heating and cooling were carried out at rates of 1.0 and 0.5 degree/minute, respectively, except where noted otherwise in parentheses.
[d]Contained 15% CH₃OH.
[e]As judged by relative retention on reverse phase (C₁₈ HPLC; elution was with 40% CH₃CN in 0.1N ammonium formate.
[f]Prepared by solid phase synthesis in analogy with the preparation of 21.
[g]From Miller et al. (1971).
[h]From Cassani and Bollum (1969).

Figure 3:
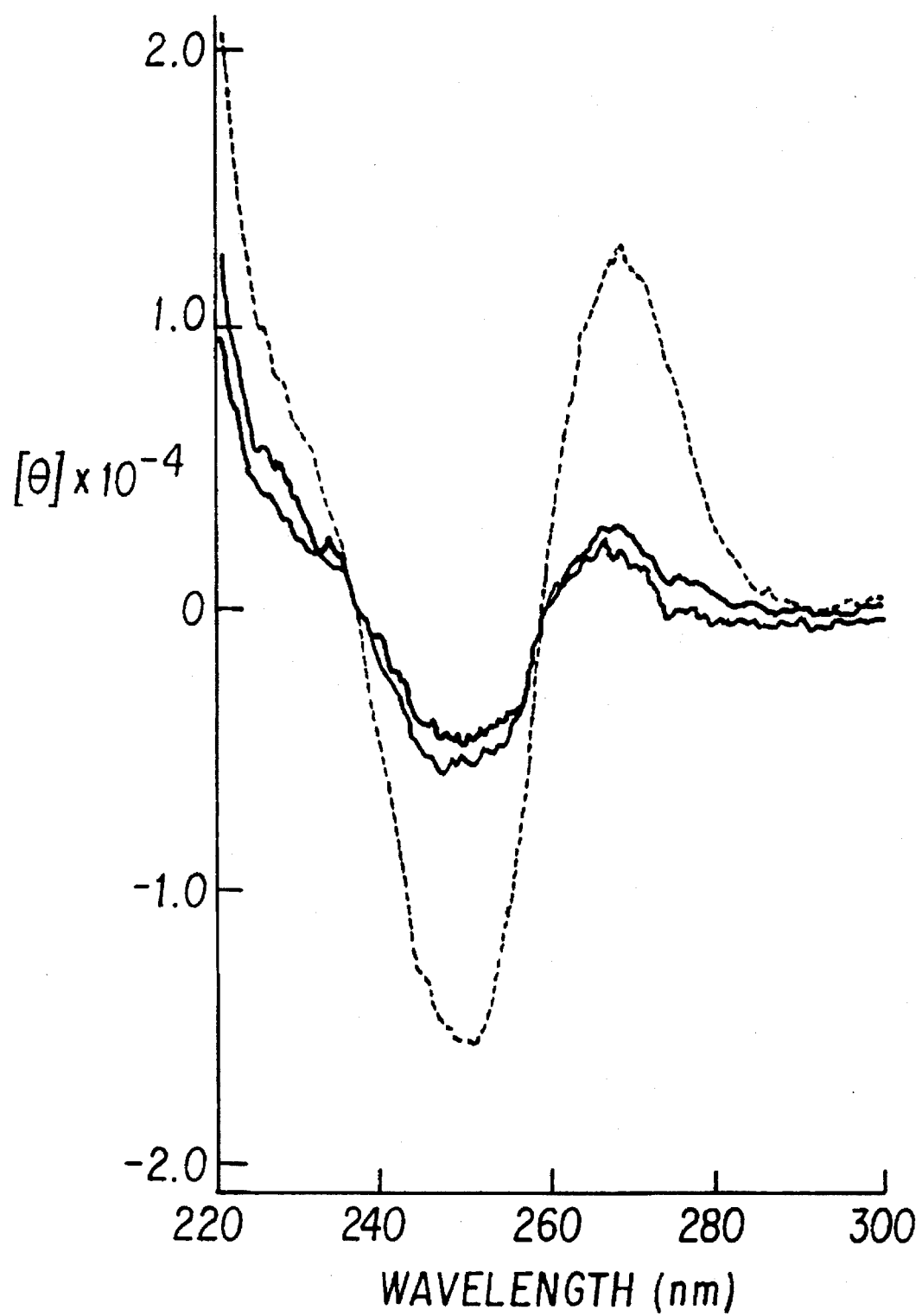
FIG. 3 provides the circular dichroic spectra d(ApA) ( . . . ), dAp($NMe_2$)dA (19f) (—), and dAp($NHC_4H_9$)dA (19c) (━━━━) in 0.01M Tris-HCl (pH 7.5)-0.01M $MgCl_2$ at 25° C. The nucleotide concentration was $6×10^{-5}$M.

The lack of dependence of alkyl chain length was also apparent in the CD spectra. As can be seen in FIG. 3, for example, the spectra of 19c and 19f were very similar. This was also true for the CD spectrum of 19d. The wavelengths of their maximum and minimum ellipticity in these spectra matched those of d(ApA), but their amplitudes were greatly reduced, as was seen with alkyl phosphotriesters (Miller et al., 1971).

Figure 4:
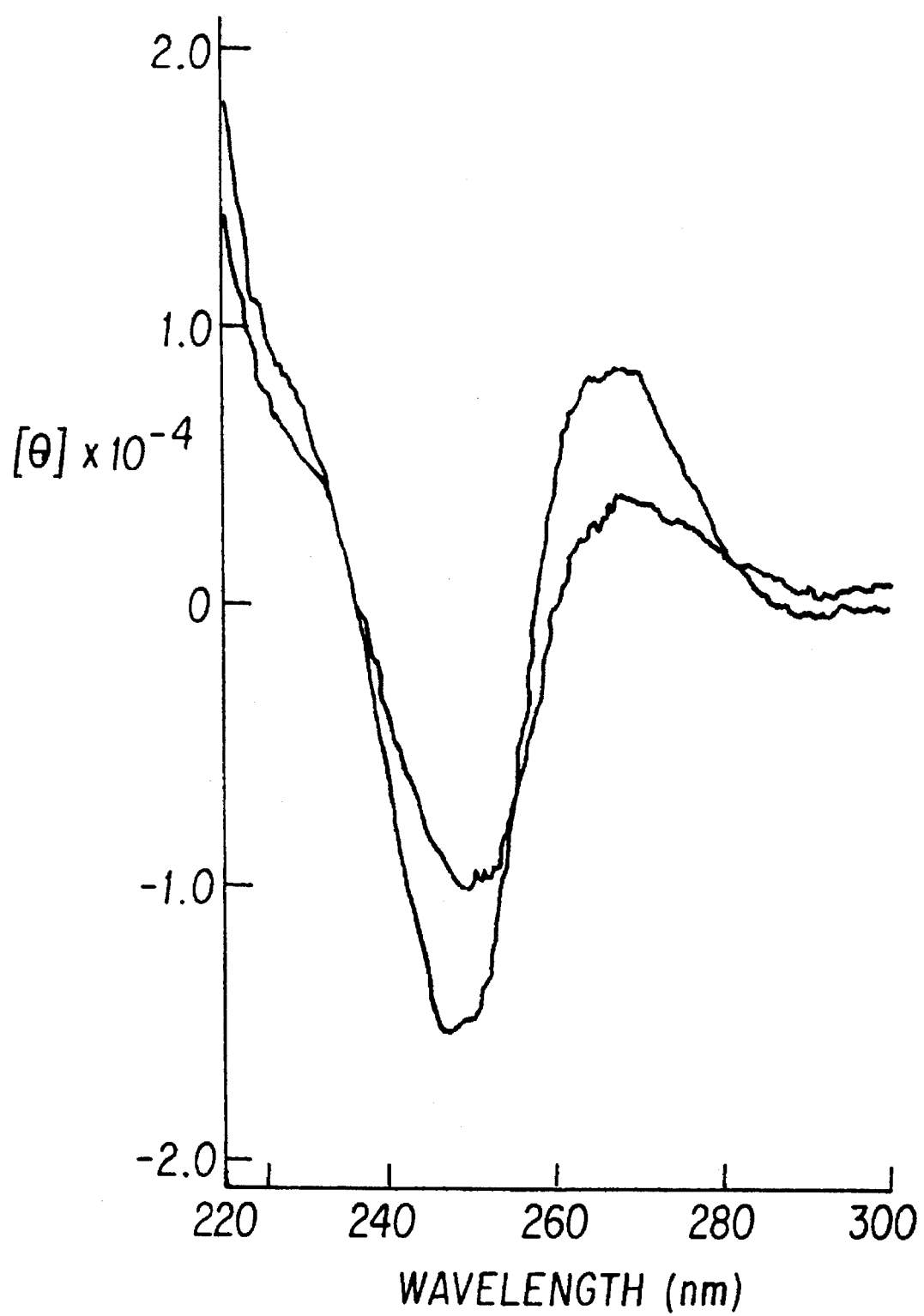
FIG. 4 provides the circular dichroic spectra of d(ApApA) (—) and d(Ap($NHC_{12}H_{25}$)ApA (━━━━) in 0.01M Tris-HCl (pH 7.5)-0.01M $MgCl_2$ at 25° C. The nucleotide concentration was $6×10^{-5}$M.

A comparison of the CD spectrum of d(ApApA) with that of d(Ap(NHC₁₂H₂₅)ApA) was also carried out. As anticipated, both spectra exhibited maximum and minimum ellipticity at the same wavelengths, but the spectrum of d(Ap(NHC₁₂H₂₅)ApA) was diminished in amplitude (FIG. 4). Both the CD and hypochromicity results are consistent with decreased interaction between adjacent bases (Kondo et al., 1970; Miller et al., 1971) in the N-alkylphosphoramidates.

Oligonucleotide Binding of Adenine Nucleoside N-Alkylphosphoramidates

Figure 5:
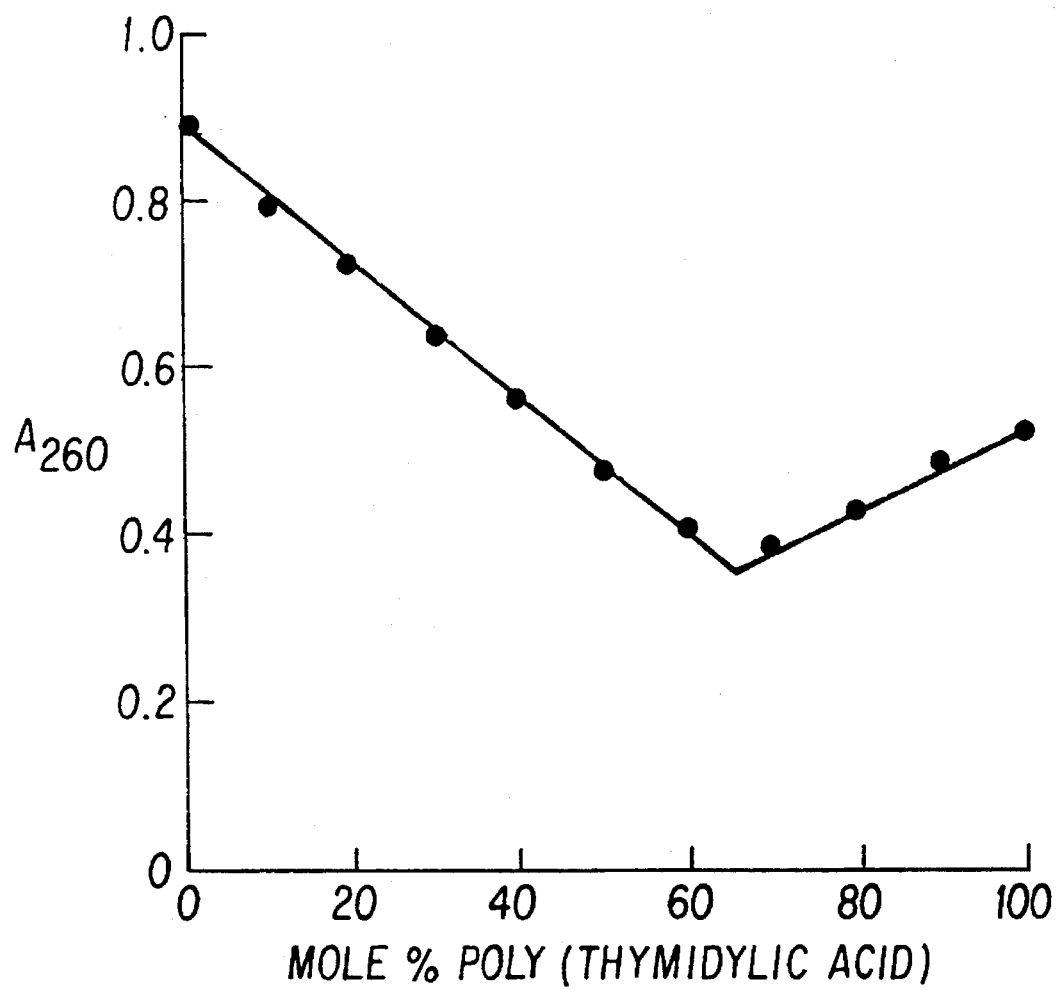
FIG. 5 provides a mixing profile of dinucleoside n-butylphosphoramidate 19c and poly(thymidylic acid). The complex was formed in 10 mM Tris-HCl, pH 7.5, containing 10 mM $MgCl_2$. Equimolar stock solutions of 19c and poly (T) ($6×10^{-5}$M nucleotide concentration) were mixed in different ratios and allowed to reach equilibrium at 0° C., after which $A_{260}$ was recorded.

The interaction of individual oligonucleotide N-alkylphosphoramidates was studied initially by the use of absorbance mixing curves. These experiments readily demonstrated the formation of complexes between oligoadenylate N-alkylphosphoramidates and poly(thymidylic acid), but not between oligothymidylate 21 and poly(dA). Accordingly, the former were studied further. As shown in FIG. 5, when measured in 10 mM Tris-HCl, pH 7.5, containing 10 mM $MgCl_2$, dinucleotide analog 19c gave an absorption minimum at 66 mole % of poly (T), corresponding to a dA:T nucleotide stoichiometry of 1:2. Since triple helix formation by polymers of adenine and thymine(uracil) nucleotides is well documented (Stevens & Felsenfeld, 1964; Davies, 1967; Tazawa et al., 1970; Miller et al., 1971; Arnott et al., 1976, Miller et al., 1981; Letsinger et al., 1986), this result was not unexpected. Essentially the same result was obtained with the other tested oligoadenylate-derived phosphoramidates.

A number of oligodenylate N-alkylphosphoramidate analogs were employed for measurements of hypochromicity and melting temperature (Table IV). The Tm values and hypochromicities in the presence of complementary oligonucleotides were determined simultaneously. In the case of 19e, 15% methanol was included to effect dissolution of the nucleotide analog.

The Tm values were determined both by heating of the formed oligonucleotide - poly (T) complexes, and by slow cooling of solutions initially maintained above the Tm. As shown in the table, the introduction of an n-butylphosphoramidate moiety in place of the phosphate ester (i.e., 19c vs. d(ApA)) resulted in a species whose binding to poly-(thymidylic acid) was altered, as judged by a substantial increase in % hypochromicity and Tm. Precisely the same effect was obtained in the presence of 15% $CH_3OH$, although the absolute values for % hypochromicity and Tm were slightly lower.

The enhanced binding of 19c to poly (T) was consistent with the observations of Letsinger et al. (1986), who found that the unsubstituted phosphoramidate of ApA also exhibited an enhanced affinity for poly (T). These authors attributed the increased binding to the absence of charge repulsion by the uncharged phosphoramidate $—NH_2$ moiety and its ability to form H bonds in aqueous media.

Also apparent in Table (V) is the effect of increasing alkyl chain length on the affinity of the oligoadenylate N-alkylphosphoramidates for poly (T). Direct comparison of d(ApA), 19c and 19e (in 15% $CH_3OH$) revealed an increase in Tm with increasing chain length. This was true for both methods of Tm determination. A significant increase in Tm was also observed when one of the phosphate esters in d(ApApA) was replaced by an N-dodecylphosphoramidate. This increase in affinity is entirely consistent with the results of Letsinger et al. (1986) who found that trichloroethyl and 1,1-dimethyltrichloroethyl esters of d(ApA) and d(ApApA) bound to poly (T) with significantly enhanced affinity. The present results suggest that lipophilic substituents may act more generally to stabilize DNA helix structure. It is worthy of note that both diastereomers of 19e had essentially the same Tm, whether measured by heating or cooling.

One interesting facet of the measurements made in the presence of poly(thymidylic acid) involved the change in % hypochromicity observed with increasing alkyl chain length (Table V). Following an initial increase in % hypochromicity as the N-alkylphosphoramidate substituent was introduced, further increases in alkyl chain length actually resulted in a decrease of the measured hypochromicity for both the di- and trinucleotide analogs studied. While the magnitude of the hypochromicity obviously reflects a complex variety of factors, the observed pattern is intriguing.

Another effect was observed in parallel with this decrease in % hypochromicity. As illustrated in Table (V), for most of the nucleotide analogs studied the Tm values were essentially identical whether determined by heating or cooling. However, for the most lipophilic di- and trinucleotide derivatives studied, the Tm's measured by heating were consistently several degrees higher than those measured by cooling. This was true for both diastereomers of 19e and for $d(Ap(NHC_{12}H_{25})ApA)$; the effect was unaltered by reasonable changes in the rate of heating or cooling. These observations suggest that the larger lipophilic substituents may cause disruption of the base stacking normally associated with polynucleotides and form duplexes that are structurally altered to permit accommodation of the liophilic substituents within the least polar regions of the formed complexes, thereby avoiding the interaction of the lipophilic groups with the polar aqueous medium. A relatively slow rate of formation and dissociation of such "disordered" oligonucleotide complexes could well be consistent with the observed differences in Tm according to the method of measurement employed.

The observed increase in affinity for a polynucleotide by its complementary oligonucleotide bearing a lipophilic alkyl substituent suggests the existence of a novel source of polynucleotide affinity. It also suggests that the alkyl groups sometimes used to covalently tether more classical DNA binding agents to polynucleotides could well be participants in the overall process by which polynucleotide binding is enhanced.

It is important to note that the present measurements were carried out with oligonucleotides of a type known form base triples readily (Stevens & Felsenfeld, 1964; Davies, 1967; Tazawa, 1970; Miller et al., 1971; Arnott et al., 1976; Miller et al., 1981; Letsinger et al., 1986); indeed the mixing profile obtained for 19c and poly (T) is suggestive of a triple strand structure. It may be the case that the novel source of affinity noted here is most readily apparent where the potential for formation of a triple strand structure exists. Indeed, this might offer some interesting opportunities for manipulation of nucleic acid structure (Moser & Dervan, 1987).

In the context of the design of sequence-specific nucleic acid probes, the oligonucleotide N-alkylphorphoramidates described here are of interest for different reasons. These include resistance to nuclease degradation, as observed upon incubation with *Penicillium citrinum* nuclease P1, and the possibility that the presence of a lipophilic alkylphosphoramidate moiety may render mammalian cells permeable to the oligonucleotide (see, e.g., Miller et al., 1985). Further, these data show that the oligonucleotide N-alkylphosphoramidate derivatives should exhibit unusual properties in systems that model DNA assembly (Behr, 1986) and encapsulation within lipid membranes (Jay & Gilbert, 1987).

Experimental Procedures:

Thymidine and tetrazole were obtained from Aldrich Chemicals. 2'-Deoxyadenosine and 3'-O-benzoylthymidine were purchased from Sigma Chemicals as were poly(dA) and poly(T). 5'-Dimethoxytrityl-2'-deoxyadenosine was obtained from Bachem. Anhydrous acetonitrile was distilled from calcium hydride and stored over 4 Å molecular sieves. Anhydrous tetrahydrofuran was heated at reflux over lithium aluminum hydride for 1 h prior to use. Oligonucleotide synthesis was carried out on a manual polynucleotide synthesizer (Matteucci & Caruthers, 1981) using Vydac TP-20 spherical silica gel (The Separations Group) as a solid support. Nuclease P1 (*Penicillium citrinum;* one unit catalyzes the hydrolysis of one µmol of phosphodiester linkages in yeast RNA in 1 min at 37° C.) and alkaline phosphatase (calf intestine; one unit catalyzes the hydrolysis of 1 µmol of p-nitrophenyl phosphate in 1 min at pH 10.4 (glycine buffer) and 37° C.) were obtained from Boehringer-Mannheim. Chromatographic separations were carried out on silica gel columns (Merck silica gel 60, 70–230 mesh (230–400 mesh for flash chromatography)) or TLC[1] plates (Merck silica gel 60, F-254, 0.2 or 2 mm thickness). HPLC analysis was carried out on an Alltech 10µ $C_{18}$ column (250×4.6 mm) using $CH_3CN-H_2O$ mixtures (either 40 mM triethylammonium acetate, pH 6.0, or 0.1M ammonium formate buffers). For preparative isolations, the appropriate fractions were collected and concentrated under diminished pressure, then diluted with water and desalted on a Bond Elut $C_{18}$ cartridge (Analytichem International).

NMR spectra were obtained on Varian EM-390 or Nicolet NT-360 spectrometers. Ultraviolet spectra were obtained on Cary 15 or 17 spectrophotometers. Circular dichroism spectra were obtained on a Jasco J-500C spectrometer. Melting profiles were obtained on a Perkin-Elmer Lambda 5 spectrophotometer.

5'-O-(Methoxytrityl)thymidine 3'-(O-methyl, N,N-diisopropylamino)phosphoramidite (15, R=MTr)

A solution containing 772 mg (1.50 mmol) of 5'-O-(p-methoxytrityl)thymidine (Schaller et al., 1963) in 8 mL of $CH_2Cl_2$ was treated with 1.75 mL (10.0 mmol) of N,N-diisopropylethylamine. Methyl (N,N-diisopropylamino)phosphorochloridite (400 µL; 2.25 mmol) was added slowly and the combined solution was maintained at 25° C. for 20 min prior to addition of 100 mL of $CH_2Cl_2$. The reaction mixture was extracted with 150 mL of saturated aqueous $NaHCO_3$ and the organic phase was dried ($Na_2SO_4$) and concentrated. The resulting foam was purified by silica gel flash column chromatography (Still et al., 1978); elution was with 6:4 $CH_2Cl_2$-hexane. The appropriate fractions were combined and concentrated under diminished pressure to afford the desired product as a gum. The product was dissolved in 6 mL of toluene and added dropwise to 200 mL of cold (−78° C.) hexane, which effected precipitation of the product as a white powder. Filtration afforded 979 mg (97%) of the activated nucleoside phosphoramidite, silica gel TLC $R_f$ 0.85 (ethyl acetate).

5'-O-(Methoxytrityl)thymidylyl(3'→5')3'-O-benzoylthymidine (2)

A solution containing 338 mg (0.5 mmol) of 5'-O-(p-methoxytrityl)thymidine 3'-(O-methyl, N,N-diisopropylamino)phosphoramidite in 2 mL of dry $CH_3CN$ was treated with 140 mg (2.0 mmol) of tetrazole and 115 mg (0.33 mmol) of 3'-O-benzoylthymidine (de Rooji et al., 1979) under $N_2$ at 25° C. for 15 min. The phosphite intermediate was oxidized by addition of an aqueous pyridine solution containing 0.1M iodine, and the reaction mixture was partitioned between $CH_2Cl_2$ and $H_2O$. The dried (($Na_2SO_4$) organic phase was concentrated and the product was purified by flash chromatography on silica gel; elution was with mixtures of $CH_2Cl_2$ and ethyl acetate. Dinucleoside monophosphate 1 was isolated as a colorless foam (~310 mg) and was employed directly for the preparation of nucleoside 2.

Demethylation of 1 was carried out by treatment with 4 mL of dioxane, 2 mL of triethylamine and 2 mL of thiophenol at 25° C. for 3 h. The reaction mixture was concentrated under diminished pressure and the residue was triturated with hexane. The residue was purified by flash chromatography on silica gel; elution was with mixtures of $CH_2Cl_2$ and $CH_3OH$ containing 1% triethylamine. The appropriate fractions were combined and concentrated, then applied to a 10-mL Amberlite IR-120 column (pyridinium form) as a methanolic solution. Elution with methanol afforded dinucleoside monophosphate 1 in quantitative yield as the pyridinium salt. The product was isolated as a powder following precipitation from a large volume of n-hexane-ether, silica gel TLC $R_f$ 0.48 (100:10:2 $CH_2Cl_2$-$CH_3OH$-triethylamine).

P-(n-Butylamino), P-deoxy-5'-O-(methoxytrityl)thymidylyl( 3'→5')(3'-O-benzoylthymidine) (3)

A mixture of 68 mg (~70 µmol) pyridinium dinucleoside monophosphate 2 and 52 mg (0.20 mmol) of triphenylphosphine was rendered anhydrous by repeated evaporations of portions of dry acetonitrile. The mixture was then dissolved in 1.5 mL of acetonitrile and 0.2 ml of dry pyridine and treated with 17 µL (27 mg; 0.18 mmol) of $CCl_4$. The reaction mixture was stirred at 25° C. for 4 h, then treated with 150 µL (110 mg; 1.5 mmol) of n-butylamine and maintained at 25° C. for an additional 30 min. The reaction mixture was concentrated under diminished pressure and the residue was purified by preparative silica gel TLC; development was with 10:1 $CH_2Cl_2$-$CH_3OH$. The product was isolated as a yellow powder, yield 16 mg.(24%); $^1$H-NMR (Table III).

P-(n-Butylamino), P-deoxy-5'-O-(methoxytrityl)thymidylyl( 3'→5')thymidine (4)

Dinucleoside monophosphate 3 (20 mg; 20 µmol) was dissolved in 2 mL of 1:1 $CH_3OH$-t-butylamine. The reaction mixture was maintained at 40°–45° C. for 2 days, then concentrated under diminished pressure. The residue was purified by preparative silica gel TLC; development was with 9:1 $CH_2Cl_2$-$CH_3OH$. Dinucleoside monophosphate 4 was isolated as an off-white gummy solid following lyophilization, yield 15 mg (84%); silica gel TLC $R_f$ 0.50 (10:1 $CH_2Cl_2$-$CH_3OH$); $^1$H-NMR ($CDCl_3$, $(CH_3)_4Si$) δ 0.8–0.9 (m), 1.2–1.35 (m), 1.32 (s), 1.81 (s), 2.1–2.9 (m), 3.00 (m), 3.4–4.3 (m), 3.71 (s), 4.4 (m), 4.6 (m), 5.04 (m), 6.07 (t), 6.35 (m), 6.78 (d), 7.2–7.4 (m), 7.50 (s) and 8.46 (br s).

Synthesis of P-(n-Butylamino), P-deoxy,5'-O-(methoxytrityl)thymidyl( 3'→5')thymidine (4) on a Solid Support A 100-mg sample of Vydac TP-20 silica gel was derivatized with ~3 µmol of fully protected dinucleoside monophosphate 5 by the method of Matteucci & Caruthers (1981). Demethylation of the phosphate ester was accomplished by treatment of the derivatized support with 2 mL of 1:2:1 triethylamine-dioxanethiophenol. The mixture was shaken at 25° C. for 3 h, then filtered and washed successively with dioxane, pyridine, methanol and ether prior to overnight drying.

The silica gel containing putative 6 was then treated with 52 mg (0.20 mmol) of triphenylphosphine, 17 µL (27 mg; 0.18 mmol) of $CCl_4$, 8 µL (8 mg; 0.1 mmol) of dry pyridine and enough dry acetonitrile to permit the mixture to be shaken at 25° C. for 3 h. The mixture was treated with 100 µL (73 mg; 1.0 mmol) of n-butylamine and maintained at 25° C. for an additional 2 h. Putative dinucleoside monophosphate 7 was treated with 3 mL of 1:1 $CH_3OH$-t-butylamine at 40° C. for 16 h. The silica gel was filtered and washed extensively with methanol. The filtrate was concentrated and the residue was purified by preparative silica gel TLC. The product (2.1 µmol; ~70% yield) was isolated as a solid $λ$max (pH 7) 268 nm. This material was shown to be identical with dinucleoside monophosphate 4 prepared via solution phase synthesis (vide supra).

Ethyl 5'-O-(Methoxytrityl)thymidine 3'-(N-n-Hexyl)phosphoramidate (9)

A solution containing 619 mg (1.20 mmol) of 5'-O-(methyoxytrityl)thymidine (Schaller et al., 1963) in 3 mL of dry tetrahydrofuran was added dropwise to a reaction vessel ($N_2$, −78° C.) containing 220 µL (343 mg; 1.30 mmol) of 2,4-dichlorophenyl phosphorodichloridite (Tolkmith, 1958), 280 µL (274 mg; 3.5 mmol) of dry pyridine and 5 mL of tetrahydrofuran. The reaction mixture was stirred at −78° C. for 10 min, then treated with 100 µL (79 mg; 1.70 mmol) of absolute ethanol and allowed to warm to room temperature. The reaction mixture was partitioned between $CH_2Cl_2$ and water, and the organic extract was dried ($Na_2SO_4$) and concentrated under diminished pressure.

Putative nucleoside 8c was dissolved in 15 mL of dry tetrahydrofuran and treated with 1.5 mL of n-hexylazide (Grundman, 1965) at 25° C. for 4 days. The reaction mixture was concentrated under diminished pressure and the residue was triturated with 30 mL of n-hexane. Purification of the crude product was effected by flash chromatography on silica gel (Still et al., 1978); elution was with increasing amounts of ethyl acetate in $CH_2Cl_2$, then with 10:1 $CH_2Cl_2$-$CH_3OH$. Ethyl 5'-O-(methoxytrityl)thymidine 3'-(N-n-hexyl)phosphoramidate (9) was isolated as a white powder, yield 373 mg (54%); silica gel TLC $R_f$ 0.47 (ethyl acetate), 0.53 (10:1 $CH_2Cl_2$-$CH_3OH$); $^1$H-NMR ($CDCl_3$, $(CH_3)_4Si$) δ 0.79 (m, 3), 1.1–1.3 (m, 11), 1.33 (s, 3), 2.2–2.9 (m, 4), 3.33 (br s, 2), 3.66 (s, 3), 3.94 (q, 2), 4.18 (m, 1), 5.02 (m, 1), 6.35 (dd, 1), 6.7–7.4 (m, 14), 7.45 (s, 1) and 9.35 (br s, 1).

Ethyl 5'-O-(Methoxytrityl)thymidine 3'-Phosphoramidato-2"-N-(glycine methyl ester)] (11)

A solution containing 129 mg (0.25 mmol) of 5'-O-(methoxytrityl)thymidine (Schaller et al., 1963) in 1.5 mL of dry tetrahydrofuran was added dropwise over a period of 5 min to a reaction vessel ($N_2$, −78° C.) containing 47 µL (73 mg; 0.28 mmol) of 2,4-dichlorophenyl phosphorodichloridite (Tolkmith, 1958), 64 µL (63 mg; 0.80 mmol) of dry pyridine and 2 mL of dry tetrahydrofuran. The reaction mixture was stirred at −78° C. for 10 min, then treated with 24 µL (19 mg; 0.40 mmol) of absolute ethanol and allowed to warm to room temperature. The reaction mixture was partitioned between $CH_2Cl_2$ and water, and the organic phase was dried ($Na_2SO_4$) and concentrated.

Putative 8c was dissolved in 3 mL of dry tetrahydrofuran and treated with 375 µL of methyl azidoacetate (Grundman, 1965) at 25° C. for 2 days. The mixture was concentrated under diminished pressure and the residue was purified by silica gel flash column chromatography; elution was with $CH_2Cl_2$ containing increasing amounts of $CH_3OH$ (up to 10%). Ethyl 5'-O-(methyltrityl)thymidine 3'-[phosphoramidato-2"-N-(glycine methyl ester)] (11) was isolated as a white powder, yield 118 mg (68%); silica gel TLC $R_f$ 0.36 (ethyl acetate), 0.50 (10:1 $CH_2Cl_2$-$CH_3Oh$); $^1$H-NMR ($CDCl_3$, $(CH_3)_4Si$) δ 1.15 (t, 3), 1.28 (s, 3), 2.0–2.6 (m, 2), 3.3–3.7 (m, 10), 3.96 (q, 2), 4.17 (m, 1), 5.09 (m, 1), 6.36 (dd, 1), 6.7–7.4 (m, 14), 7.47 (s, 1) and 9.39 (br s, 1).

Ethyl 5'-O-(Dimethoxytrityl)thymidine 3'-(N-n-Butyl)phosphoramidate (13)

A solution containing 338 mg (0.62 mmol) of 5'-O-(dimethoxytrityl)thymidine (Schaller et al., 1963) in 1.8 mL of dry tetrahydrofuran was added dropwise to a reaction vessel ($N_2$, −30° C.) containing 57 µL (80 mg; 0.60 mmol) of methyl phosphorodichoridite (Martin & Pizzolato, 1950), 160 µL (158 mg; 2.0 mmol) of dry pyridine and 4 mL of tetrahydrofuran. The reaction mixture was stirred at −30° C. for 5 min, then treated with 100 µL (79 mg; 1.70 mmol) of absolute ethanol. The reaction mixture was allowed to warm to 0° C., then added to ice water and extracted with portions of $CHCl_3$. The combined $CHCl_3$ extract was dried ($Na_2SO_4$) and concentrated. Putative nucleoside phosphite derivative 12 was dried carefully by coevaporation of portions of dry toluene and tetrahydrofuran, then treated with a solution containing 200 mg (0.8 mmol) of iodine in 2 mL of dry tetrahydrofuran +1 mL of n-butylamine. The reaction mixture was stirred at 25° C. for 5 min, then partitioned between $CHCl_3$ and aqueous $NaHSO_3$. The organic extract was dried ($Na_2SO_4$) and concentrated under diminished pressure. The residue was purified by silica gel flash chromatography (20-g column); elution was with 0–2% $CH_3OH$ in ethyl acetate. Ethyl 5'-O-(dimethoxytrityl)thymidine 3'-(N-n-butyl phosphoramidate (13) was obtained as a white solid by precipitation from a large volume of hexane, yield 196 mg (45%); silica gel TLC $R_f$ 0.26 (ethyl acetate), 0.50 (20:1 $CHCl_3$-$CH_3OH$); $^1$H-NMR ($CDCl_3$, $(CH_3)_4Si$) 0.8 (t, 3), 1.05–1.2 (m, 10), 2.15–2.9 (m, 4), 3.32 (br s, 2), 3.67 (s, 6), 3.88 (q, 2), 4.15 (m, 1), 5.00 (m, 1), 6.35 (dd, 1), 6.65–7.3 (m, 13), 7.49 (s, 1) and 9.03 (s, 1).

Nucleoside phosphoramidate 13 was characterized further by $^1$H-NMR following deprotection (81% yield) with 80% aqueous HOAc.

General Procedure for the Preparation of Dinucleoside Phosphoramidates (17)

In a typical experiment, 0.3 mmol of 5'-hydroxy- 3'-O-benzoylated nucleoside (16) (Eckstein, 1967; Ogilvie, 1973) was treated with 0.40–0.45 mmol of nucleoside 3'-(O-methyl, N,N-diisopropylamino)phosphoramidite (15) in 1.5 mL of dry acetonitrile containing 1.6–2.0 mmol of tetrazole. The reaction mixture was maintained at 25° C. for 20–30 min, then partitioned between $CH_2Cl_2$ and water. The $CH_2Cl_2$ layer was dried ($Na_2SO_4$) and concentrated under diminished pressure. After codistillation of several portions of dry tetrahydrofuran from the residue, the resulting foam was dissolved in 2 mL of dry tetrahydrofuran and treated with 0.40–0.45 mmol of iodine in 2 mL of tetrahydrofuran and 1 mL of alkylamine. After 5 min, the reaction mixture was poured into aqueous sodium bisulfite and extracted with portions of $CH_2Cl_2$. The $CH_2Cl_2$ extract was dried ($Na_2SO_4$) and concentrated.The residue was purified by silica gel flash chromatography (Still et al., 1978) or by preparative silica gel TLC using $CH_2Cl_2$-$CH_3OH$ mixtures.

In this fashion, 0.45 mmol (304 mg) of 5'-O-(methoxytrityl)thymidine 3'-(O-methyl, N,N-diisopropylamino)phosphoramidite and 0.30 mmol (114 mg) of 3'-O-benzoylthymidine afforded P-deoxy, P-(n-octylamino)-5'-(O-methoxytrityl)thymidylyl(3'→5')(3'-O-benzoylthymidine (17a) as a white solid following chromatographic purification and precipitation from a large volume of 2:1 hexane-ether, yield 237 mg (76%); silica gel TLC $R_f$ 0.36 and 0.43 (ethyl acetate), 0.32 and 0.36 (10:1 $CH_2Cl_2$-$CH_3OH$); $^1$H-NMR ($CDCl_3$, $(CH_3)_4Si$) δ 0.87 (t), 1.2–1.3 (m), 1.37 (s), 1.5 (m), 1.92 (s), 1.94 (s), 2.2–3.0 (m), 3.3–3.6 (m), 3.77 (s), 3.79 (s), 4.2–4.4 (m), 5.15 (m), 5.47 (d), 5.56 (d), 6.3–6.5 (m), 6.8–6.9 (2d), 7.2–7.6 (m), 7.53 (s), 8.0 (2d) and 8.4 (br s). The yields of the other dinucleoside phosphoramidates prepared is given in Table I; $^1$H-NMR values for these compounds is also provided (Table IV) supra.

Virtually identical yields of these products were obtained in one-pot procedures that omitted isolation of the intermediate dinucleoside phosphites.

General Procedure for Deprotection of Dinucleoside Phosphoramidates (17)

In a typical experiment, 0.1 mmol of the fully protected dinucleoside phosphoramidate was debenzoylated to afford 18 by stirring overnight with 10 mL of 1:1 t-butylamine-methanol at 45°–50° C. The solvent was removed under diminished pressure and the residue was purified by silica gel flash chromatography or by preparative silica gel TLC using $CH_2Cl_2$-$CH_3OH$ mixtures. Detritylation was effected by treatment with 2 mL of 80% aqueous acetic acid at 25°

C. for 1 h (dimethoxytrityl derivatives) or 16 h (monomethoxytrityl derivatives), affording deprotected dinucleoside phosphoramidate 19. Following removal of acetic acid under diminished pressure the residue was co-evaporated with portions of toluene and then purified by preparative silica gel TLC (development with $CH_2Cl_2$-$CH_3OH$ mixtures).

In this fashion, 100 μmol (104 mg) of P-deoxy, P-(n-octylamino)-5'-O-(methoxytrityl)thymidylyl( 3'→5')(3'-O-benzoylthymidine) (17a) was deprotected to provide P-deoxy, P-(n-octylamino)thymidylyl( 3'→5')thymidine (19a) as a white solid following preparative silica gel TLC (10:1 $CH_2Cl_2$-$CH_3OH$) and lyophilization from dioxane, yield 53 mg (77%); silica gel TLC $R_f$ 0.07 (10:1 $CH_2Cl_2$-$CH_3OH$), 0.60 (5:1 $CH_2Cl_2$-$CH_3OH$); $^1$H-NMR ($CDCl_3$, $(CH_3)_4Si$) δ 0.87 (t), 1.3 (m), 1.5 (m), 1.90 (s), 1.92 (s), 2.1–2.9 (m), 3.6 (m), 3.8 (m), 4.0–4.2 (m), 4.45 (m), 5.08 (m), 6.30 (dd), 7.32 (s), 7.41 (s)and 7.68 (s). The yields of the other dinucleoside phosphoramidates prepared is given in Table I; $^1$H-NMR values for these compounds is also summarized (Table IV).

Synthesis of TpTpTpT Phosphoramidates 20–22

The requisite tetrathymidylate derivatives were prepared on a manual polynucleotide synthesizer as described by Matteucci and Caruthers, (1981). Derivatized silica gel (71 μmol DMTr groups/g silica gel) was used in 400-mg columns. Individual couplings were carried out as described (Matteucci & Caruthers, 1981) using 5'-O-(dimethoxytrityl)thymidine 3'-(O-methyl, N,N-diisopropylamino)phosphoramidite+ tetrazole in tetrahydrofuran. Oxidation of individual phosphite bonds was also carried out as described using 0.1M $I_2$ in 2:1:1 tetrahydrofuran-$H_2O$-lutidine, except that introduction of the N-alkylphosphoramidate linkage was accomplished by substitution of 0.1M $I_2$ in 2:1 tetrahydrofuran-alkylamine for introduction of the appropriate internucleotide bond.

After completion of each tetranucleotide synthesis the silica gel containing the fully protected tetranucleotide was treated with 2 mL of 2:1:1 dioxane-thiophenol-triethylamine at 25° C. for 90 min. The silica gel was washed successively with dioxane, $CH_3OH$ and $CH_2Cl_2$, after which the tetranucleotide was hydrolyzed from the support by treatment overnight with 2 mL of 1:1 t-butylamine-$CH_3OH$ at 45° C. and the tritylated oligomers were purified by preparative HPLC on a 10μ $C_{18}$ column; elution was effected with 0.04M triethylammonium acetate, pH 6.9, containing 35% (for DMTr - 22), 38% (for DMTr - 20) or 51% (for DMTr -21) acetonitrile. Purification by HPLC also effected separation of the diastereomers (retention times: 10.9 and 15.8 min for DMTr - 20; 9.7 and 12.5 min for DMTr - 21; 10.3 and 14.0 min for DMTr - 22). Approximately 20% of each crude tetranucleotide preparation was purified by HPLC, yielding at each case ~8 $A_{260}$ units of the individual diastereomers.

Deprotection of individual diastereomers of DMTr - 20–22 was carried out with 1 mL of 80% aqueous HOAc at 25° C. overnight. The solvent was concentrated under diminished pressure and the residue was co-evaporated with portions of toluene and triturated with ether. Purification was effected by $C_{18}$ reverse phase HPLC using $CH_3CN$ in 0.04M triethylammonium acetate, pH 6.9. Approximately 5 $A_{260}$ units of each tetranucleotide was obtained.

Enzymatic Digestion of TpTpTpT Phosphoramidates 20–22

Digestion of tetranucleotides 20–22 (0.1–0.2 $A_{260}$ unit scale) was carried out in 100 μL of 0.25M Tris.HCl, pH 7.0, containing 6–9 units of *Pencillium citrinium* nuclease P1. The digestions were carried out at 37° C. for 4 h, and one half of the reaction mixtures were analyzed by HPLC. The remaining half of each reaction mixture was combined with 2 units of calf intestine alkaline phosphatase and incubated for an additional 30 min prior to HPLC analysis.

Also analyzed in the same fashion was a diastereomeric mixture of P-(n-butylamino), P-deoxythymidylyl( 3'→5')thymidine.

6-Chloro-9-(p-chlorophenoxy)-2-methoxyacridine

A reaction mixture consisting of 1.39 g (5.0 mmol) of 6,9-dichloro-2-methoxyacridine and 3.0 g (23 mmol) of p-chlorophenol was heated at 80° C. for 4 h. The hot reaction mixture was poured into hot 5% aqueous NaOH. The combined solution was stirred until a fine yellow crystalline precipitate appeared. The crystals were filtered, washed to neutrality with water and dried at 70° C. in vacuo. Recrystallization from pyridine afforded 6-chloro-9-(p-chlorophenoxy)-2-methoxyacridine as yellow microcrystals, yield 1.06 g (57%), mp 151.5°– 153° C.; $\lambda_{max}$ ($CH_3OH$) 400, 381, 351, 333, 318 (sh) and 262 nm; $^1$H-NMR ($CDCl_3$, $(CH_3)_4Si$) δ 3.76 (s, 3) 6.7–6.9 (m, 2) 7.1–7.6 (m, 5) and 7.8–8.2 (m, 3).

P-(5-Aminopentylamino), P-deoxy-5'-O-(methoxytrityl)thymidylyl( 3'→5') (3'-O-methoxytritylthymidine) (24)

A solution containing 370 mg (0.55 mmol) of 5'-O-(methoxytrityl)thymidine 3'-O-methyl, N,N-diisopropylamino)phosphoramidite (15, R=MTr) in 2 mL of dry acetonitrile was treated with 178 mg (2.5 mmol) of tetrazole and 232 mg (0.45 mmol) of 3'-methoxytritylthymidine (Ogilvie & Letsinger, 1967, Matteucci & Caruthers, 1980). The reaction mixture was maintained at 25° C. for 20 min, then treated with 125 mg (0.49 mmol) of iodine in 3 mL of 2:1 tetrahydrofuran- 1,5-diaminopentane. After 5 min at 25° C., the reaction mixture was concentrated under diminished pressure and the residue was partitioned between $CH_2Cl_2$ and 50% aqueous methanol. The organic phase was dried ($Na_2SO_4$) and concentrated. The residue was purified by silica gel flash chromatography (30-g column); elution was carried out using $CH_2Cl_2$ containing increasing amounts of methanol. In this fashion each of the diastereomers of P-(5-aminopentylamino), P-deoxy-5'-O-(methoxytrityl)thymidylyl( 3'→5)(3'-O-methoxytritylthymidine) (24) was obtained as an off-white powder in chromatography homogeneous form, yield 125 mg (24%) of the less polar isomer (silica gel TLC $R_f$ 0.48 (5:1 $CH_2Cl_2$-$CH_3OH$)) and 166 mg (31%) of the more polar isomer ($R_f$ 0.43); $^1$H-NMR (less polar isomer) ($CDCl_3$, $(CH_3)_4Si$) δ 1.38 (s), 1.78 (s), 1.2–2.0 (m), 2.2–2.8 (m), 3.2–3.7 (m), 3.75 (s), 3.78 (s), 3.9–4.3 (m), 5.03 (br t), 6.17 (t), 6.33 (dd), 6.83 (dd), 7.2–7.5 (m), 7.50 (s) and 8.38 (s). $^1$H-NMR (more polar isomer) δ 1.34 (s), 1.77 (s), 1.2–1.8 (m), 2.2–2.9 (m), 3.3–3.7 (m), 3.75 (s), 3.77 (s), 3.9–4.2 (m), 5.08 (br t), 6.22 (t), 6.33 (dd), 6.8–6.9 (m), 7.2–7.4 (m), 7.54 (s), and 8.42 (s).

P-(5-(6'-Chloro-2'-methoxyacridin-9'-yl)aminopentylamino), P-deoxy-thymidylyl(3'→5')thymidine (26)

To solutions of 118 mg (0.10 mmol) of each of the diastereomers of 24 in 400 μL of pyridine was added 167 mg (0.45 mmol) of 6-chloro-9-(p-chlorophenoxy)-2-methoxyacridine and the reaction mixtures were heated overnight at 60° C. Each reaction mixture was diluted with $CH_3OH$, filtered to remove insoluble material and concentrated under diminished pressure. The yellow solid product obtained from each was purified by preparative silica gel TLC, development with 9:1 $CH_2Cl_2$-$CH_3OH$. The individual diastereomers (putative 25) were treated separately with 6 mL of 2% trifluoroacetic acid in $CH_2Cl_2$ (30 min, 25° C.) to effect ditritylation. The individual diastereomers were isolated as yellow powders following precipitation of each from a large volume of ether as the presumed trifluoroacetate salt, yield 63 mg (64%) of the less polar isomer; 53 mg (54%) of the more polar isomer; $^1$H-NMR (less polar isomer) (CDCl$_3$, DMSO-d$_6$) δ 1.2–1.4 (m), 1.78 (s), 2.0–2.8 (m), 3.65 (s), 3.84 (t), 3.92 (s), 4.0–4.1 (m), 4.28 (m), 4.5 (br s), 4.95 (t, 1), 6.22 (q, 2), 7.6–7.7 (m), 7.79 (d, 1), 7.84 (s) and 8.23 (d). $^1$H-NMR (more polar isomer) δ 1.2–1.6 (m), 1.90 (d), 2.0–2.6 (m), 3.8–4.2 (m), 3.92 (s), 4.4 (br s), 4.6 (br s), 5.05 (m), 6.3 (m), 7.6–7.7 (m), 7.79 (d), 7.84 (s) and 8.23 (d).

Compound 26 was also prepared on a solid support in analogy with the synthesis of n-alkylphosphoramidates 20–22.

Determination of Melting Temperatures for Complexes of Oligoadenylate Analogs and Poly (T)

Solutions of both the oligonucleotides and poly-(thymidylic acid) were prepared at nucleotide concentrations of 6×10$^{-5}$M, and mixed in a nucleotide ratio of 1:2 (dA: T) in 10 mM Tris-HCl, pH 7.5, containing 10 mM MgCl$_2$. In some cases, 15% CH$_3$OH was added to facilitate dissolution of oligonucleotide N-alkylphosphoramidates. The spectroscopic behavior upon cooling or heating was monitored by UV at 260 nm. Hypochromicities of individual oligonucleotide analogs were determined as described (Tazawa et al., 1970; Miller et al., 1981). Molar extinction coefficients of 8.52×10$^3$ (264 nm) for poly (T) and 9.39×10$^3$ (257 nm) for poly(dA) were used.

References

Acheson, R. M. (1973) "The Chemistry of Heterocyclic Compounds: Acridines", Interscience Publishers, Inc., New York, p. 113.

Agris, C. H., Blake, K. R., Miller, P. S., Reddy, M. P. and Ts'o, P. O. P. (1986) *Biochemistry* 25, 6268.

Albert, A. and Ritchie, B. (1943) *J. Chem. Soc.*, 458.

Appel, R. (1975) Agnew. Chem. Int. Ed. Engl. 14, 801–811

Arnott, S., Bond, P. J., Selsing, E., & Smith, P. J. C. (1976) *Nucleic Acids Res.* 3, 2459–2470.

Asseline, U., Toulme, F., Thuong, N. T., Delavue, M., Montenay-Garestier, T., & Helene, C. (1984) *EMBO J.* 3, 795–800.

Asseline, U., Tolme, F., Thuong, N. T., Delavue, M., Montenay-Garestier, T. and Helene, C. (1984) *EMBO J.* 3, 795.

Baker, B. F. and Dervan, P. B. (1985) *J. Am. Chem. Soc.* 107, 8266.

Bajwa, G. S., & Bentrude, W. S. (1978) Tetrahedron Lett., 421–424.

Barnes, D. M. (1987) *Science* 236, 1423

Barr, P. J., Power, M. D., Lee-Ng, C.-T., Gibson, H. L. and Luciw, P. A. (1987) *Bio/Technology* 5, 486.

Barre-Sinoussi, F., Chermann, J. C., Rey, F., Nugeyre, M. T., Chamaret, S., Gruest, Jr., Dauguet, C., Axler-Blin, C., Vezinet-Brun, F., Rouzioux, C., Rozenbaum, W. and Montagnier, L. (1983) *Science* 220, 868.

Behr, J.-P. (1986) Tetrahedron Lett. 27, 5861–5864.

Blake, K. R., Murakami, A., and Miller, P.S. (1985a) *Biochemistry* 24, 6132.

Blake, K. R., Murakami, A., Spitz, S. A., Glave, S. A., Reddy, M. P., Ts'o, P. O. P. and Miller, P. S. (1985b) *Biochemistry* 24, 6139.

Boidot-Forget, M., Thuong, N. T., Chassignol, M., & Helene, C. (1986) C. R. *Acad. Sci. Ser.* 3 302, 75–80.

Boidet-Forget, M., Chassignol, M., Francois, J. C., Helene, C., Le Doan, T., Perrouault, L., Saison-Behmoaras, T., & Thuong, N. T. (1987) *Rec. Trav. Chim. Pays-Bas.* 106, 189.

Boutorin, A., Vlassov, V. V., Koyakov, S. A., Kutiavin, I. V., & Podyminoyin, M. A. (1984) FEBS Lett. 172, 43–46.

Boidot-Forget, M.; Thuong, N. T., Chassignol, M., Helene, C. (1986) *C. R. Acad. Sci.* Ser 3, 302, 75.

Cassani, G. R. & Bollum, F. J. (1969) *Biochemistry* 8, 3928–3936.

Cazenave, C., Loreau, N., Toulme, J. J. and Helene, C. (1986) *Biochimie* 68, 1063.

Cech, T. R. and Bass, B. L. (1986) *Annu. Rev. Biochem.* 55, 599.

Chandra, A., Gerber, T. and Chandra, P. (1986) *FEBS Lett.* 197, 84.

Cheng, Y., Dutschman, G. E., Bastow, K. F., Sarngadharan, M. G., and Ting, R. Y. C. (1987) *J. Biol. Chem.* 262, 2187.

Chu, C. F., & Orgel, L. E. (1985) *Proc. Natl. Acad. Sci. USA* 82, 963–967.

Chu, B. C., Wahl, G. M., Orgel, L. E. (1983) *Nucleic Acids Res.* 11, 6513.

Chu, C. F. and Orgel, L. E. (1985) *Proc. Natl. Acad. Sci. USA* 82, 963.

Conner, B. J., Reyes, A. A., Morin, C., Itakura, K., Teplitz, R. L. and Wallace, R. B. (1983) *Proc. Natl. Acad. Sci. USA* 80, 278.

Connolly, B. A., Potter, B. V. L., Eckstein, F., Pingoud, A., & Grotjahn, L., (1984) *Biochemistry* 23, 3443–3453.

Cramer, F., Freist, W., Schattka, K., & Jastorff, B. (1972) *Chem. Ber.* 105, 991–999.

Davies, D. R. (1967) *Annu. Rev. Biochem.* 36, 321–364.

Dayton, A. L., Sodroski, J. G., Rosen, C. A., Goh, W. C. and Haseltine, W. A. (1986) *Cell* 44, 941.

de Rooji, J. F. M., Jr., Wilhe-Hazeleger, G., van Deursen, P. H., Serdijn, J., &.van Boom, J. H. (1979) *Rec. Tray. Chim. Pays-Bas* 98, 537–548.

Doan, T. L., Perrouault, L., Helene, C., Chassignol, M., and Thuong, N. T. (1986) *Biochemistry* 25, 6736.

Dreyer, G. B. & Dervan, P. B. (1985) *Proc. Natl. Acad. Sci. USA* 82, 968–972.

Dreyer, G. B. and Dervan, P. B. (1985) *Proc. Natl. Acad. Sci. USA* 82, 968.

Eckstein, F. (1967) *Chem. Ber.* 100, 2228–2235.

Edwards, M. L., Bambury, R. E. and Ritter, H. W. (1975) *J. Med. Chem.* 18, 637.

Farmerie, W. G., Loeb, D. D., Casavant, N. C., Hutchison, C. A., III, Edgell, M. H. and Swanstrom, R. (1987) *Science* 236, 305.

Fisher, A. G., Feinberg, M. B., Josephs, S. F., Harper, M. E. Marselle, L. M., Reyes, G., Gonda, M. A., Aldovini, A., Debouk, C., Gallo, R. C. and Wong-Staal, F. (1986) *Nature* 320, 367.

Froehler, B. C. (1986) Tetrahedron Lett. 27, 5575–5578.

Grundman, C. (1965) in Houben-Weyl, Methoden der Organischer Chemie (Muller, E., Ed.), Vol. IV, 3, p 792–796, 3rd Ed., G. Thieme Verlag, Stuttgart.

Hecht, S. M. (1986) *Accounts Chem. Res.* 19, 383.

Helene, C., Montenay-Garestier, T., Saison, T., Takasugi, M., Toulme, J. J., Asseline, U., Lancelot, G., Maurizot, J. C. Toulme, F. and Thuong, N. T. (1985) *Biochemie* 67, 777.

Helene, C., Montenay-Garestier, T., Saison, T., Takasugi, M., Toulme, J. J., Asseline, U., Lancelot, G., Maurizot, J. C., Toulme, F., & Thuong, N. T. (1985) *Biochimie* 67, 777–783.

Hertzberg, R. P. and Dervan, P. B. (1982) *J. Am. Chem. Soc.* 104, 313.

Itakura, K., and Riggs, A. D. (1980) *Science* 209, 1401.

Iverson, B. L., & Dervan, P. B. (1987) *J. Am. Chem. Soc.* 109, 1241–1243.

Iverson, B. L. and Dervan, P. B. (1987) *J. Am. Chem. Soc.* 109, 1241.

Izant, J. G. and Weintraub, H. (1984) *Cell* 36, 1007.

Jay, D. G., & Gilbert, W. (1987) *Proc. Natl. Acad. Sci. USA* 84, 1978–1980.

Juodka, B. A. & Smrt, J. (1974) *Collect. Czech. Chem. Commun.* 39, 963–968.

Kehrmann, F. and Prunier, P. (1924) *Helv. Chim. Acta.* 7, 472.

Knight, D., M., Flomerfelt, F. A. and Ghrayeb, J. (1987) *Science* 236, 837.

Knorre, D. G., Vlassov, V. V., Zarytova, V. F., & Karpova, G. G. (1985a) *Adv. Enzyme Regulation* 24, b 277–299.

Knorre, D. G., Vlassov, V. V. (1985b) *Prog. Nucleic Acid Res. Mol. Biol.* 32, 291–320.

Knorre, D. G., Vlassov, V. V., Zarytova, V. F. and Karpova, G. G. (1985a) *Adv. Enzyme Regulation* 24, 277.

Knorre, D. G. and Vlassov, V. V. (1985b) *Prog. Nucleic Acid Res. Mol. Biol.* 32, 291.

Kondo, N. S., Holmes, H. M., Stempel, L. M. & Ts'o, P. O. P. (1970) *Biochemistry* 9, 3479–3498.

Laderoute, K. R. and Rauth, A. M. (1986) *Biochem. Pharmacol.* 35, 3417.

Lancelot, G. and Thuong, N. T. (1986) *Biochemistry* 25, 5357.

Larder, B. A., Purifoy, D. J. M., Powell, K. L. and Darby, G. (1987) *Nature* 327, 716.

Laurence, J., Saunders, A. and Kulkosky, J. (1987) *Science* 235, 1501.

Le Doan, T., Perrouault, L., Helene, C., Chassignol, M., & Thuong, N. T. (1986) *Biochemistry* 25, 6736–6739.

Letsinger, R. L., & Schott, M. E. (1981) *J. Am. Chem. Soc.* 103, 7394–7396.

Letsinger, R. L., Bach, S. A., & Eadie, J. S. (1986) *Nucleic Acids Res.* 14, 3487–3499.

Letsinger, R. L. and Schott, M. E. (1981) *J. Am. Chem. Soc.*, 103, 7394.

Levy, J. A., Hoffman, A. D., Kramer, S. M., Landis, J. A., Shimabukuro, J. M. and Oshiro, L. S. (1984) *Science* 225, 840.

Martin, D. R., & Pizzolato, P. J. (1950) *J. Am. Chem. Soc.* 72, 4584–4586.

Matteucci, M. D., & Caruthers, M. H. (1980) *Tetrahedron Lett.* 21, 3243–3246.

Matteucci, M. D. & Carthers, M. H. (1981) *J. Am. Chem. Soc.* 103, 3185–3191.

Matteucci, M. D. and Caruthers, M. H. (1980) *Tetrahedron Lett.* 21, 3243.

Maxam, A. M. and Gilbert, W. (1980) *Methods Enzymol.* 65, 499.

Meyer, Jr., R. B., Shuman, D. A., & Robins, P. K. (1973) *Tetrahedron Lett.*, 269–272.

Mevarech, M., Noyes, B. E. and Agarwal, K. L. (1979) *J. Biol. Chem.* 254, 7472.

Miller, P. S., Agris, C. H., Aurelian, L., Blake, K. R., Murakami, A., Reddy, M.P., Spitz, S. A., & Ts'o, P. O. P. (1985) *Biochemie* 67, 769–776.

Miller, P. S., Fang, K. N., Kondo, N. S., & Ts'o, P. O. P. (1971) *J. Am. Chem. Soc.* 93, 6657–6665.

Miller, P. S., McParland, K. B., Jayaraman, K., & Ts'o, P. O. P. (1981) *Biochemistry* 20, 1874–1880.

Miller, P. S., Agris, C. H., Aurelian, L., Blake, K. R., Murakami, A., Reddy, M. P., Spitz, S. A. and Ts'o, P. O. P. (1985) *Biochemie* 67, 769.

Miller, P. S., Agris, C. H., Blandin, M., Murakami, A., Reddy, P. M., Spitz, S. A and Ts'o P. O. P. (1983a) *Nucleic Acids Res.* 11, 5189

Miller, P. S., Agris, C. H., Murakami, A., Reddy, P. M., Spitz, S. A and Ts'o, P. O. P., (1983b) *Nucleic Acids Res.* 11, 6225.

Moser, H. E., & Dervan, P. B. (1987) *Science* 238, 645–650.

Murakami, A., Blake, K. R. and Miller, P. S. (1985) *Biochemistry* 24, 4041.

Naylor, R., and Gilham, P. T. (1966) *Biochemistry* 5, 2722.

Nemer, M. J., & Ogilvie, K. K. (1980) *Tetrahedron Lett.* 21, 4149–4152.

Noyes, B. E., Mevarech, M., Stein, R., and Agarwal, K. L. (1979) *Proc. Natl. Acad. Sci. USA* 76, 1770.

Ogilvie, K. K., & Letsinger, R. L. (1967) *J. Org. Chem.* 32, 2365–2366.

Ogilvie, K. K. (1973) *Can J. Chem.* 51, 3799–3807

Payne, R. C., Nichols, B. P. and Hecht, S. M. (1987) *Biochemistry* 26, 3197.

Peattie, D. A. (1979) *Proc. Natl. Acad. Sci. USA* 76, 1760.

Peattie, D. A. and Gilbert, W. (1980) *Proc. Natl. Acad. Sci. USA* 77, 4679.

Peattie, D. A. and Herr, W. (1981) *Proc. Natl. Acad. Sci. USA* 78, 2273.

Peattie, D. A., Douthwaite, S., Garrett, R. A. and Noller, H. F. (1981) *Proc. Natl. Acad. Sci USA* 78, 7331.

Peattie, D. A. (1983) in: Techniques in the Life Sciences, B509, Elsevier Scientific Publishers Ireland Ltd., pl-ff.

Pestka, S., Daugherty, B. L., Jung, V., Hotta, K., and Pestka, R. K. (1984) *Proc. Natl. Acad. Sci. USA* 81, 7525.

Popovic, M., Sarngadharan, M. G., Read, E., and Gallo, R. C. (1984) *Science* 224, 497.

Pramanik, P. and Kan, L. (1987) *Biochemistry* 26, 3807.

Rordorf, B. F. and Kearns, D. F. (1976) *Biopolymers* 15, 1491.

Rosenberg, U. B., Preiss, A., Seifert, E., Jackle, H., and Knipple, D. C. (1985) *Nature* 313, 703.

Schaller, H., Weimann, G., Lerch, B., & Khorana, H. G. (1963) *J. Am. Chem. Soc.* 85, 3821–3827.

Schultz, P. S. and Dervan, P. B. (1983a) *Proc. Natl. Acad. USA* 80, 6834.

Schultz, P. S. and Dervan, P. B. (1983b) *J. Am. Chem. Soc.* 105, 7748.

Schofield, P. and Zamecnik, P. C. (1968) *Biochim. Biophys. Acta* 155, 410.

Sodroski, J., Goh, W. C., Rosen, C., Dayton, A.,

Stec, W. J. (1983) *Acc. Chem. Res.* 16, 411–417.

Stephenson, M. L. and Zamecnik, P. C. (1978) *Proc. Natl. Acad. Sci. USA* 75, 285.

Stevens, C. L., & Felsenfeld, G. (1964) *Biopolymers* 2, 293–314.

Still, W. C., Kahn, M., & Mitra, A. (1978) *J. Org. Chem.* 43, 2923–2925.

Swan, G. A. and Felton, D. G.I. (1957a) "The Chemistry of Heterocyclic Compounds: Phenazines", Interscience Publishers Inc., New York, p. 19.

Swan, G. A. and Felton, D. G. I. (1957b) *Ibid., p.* 67, 68.

Tanese, N., Sodroski, J., Haseltine, W. A. and Goff, S. P. (1986) *J. Vivol.* 59, 743.

Tazawa, I., Tazawa, S., Stempel, L. M., & Ts'o, P. O. P. (1970) *Biochemistry* 9, 3499–3514.

Terwilliger, E. and Haseltine, W. (1986) *Nature* 321, 413.

Thuong, N. T., Asseline, U., Roig, V., Takasugi, M., & Helene, C. (1987) *Proc. Natl. Acad. Scio USA* 84, 5129–5133.

Tolkmith, H. (1958) *J. Org. Chem.* 23, 1682–1684.

Toulme, J. J., Krisch, H. M., Loreau, N., Thuong, N. T., & Helene, C., (1986) *Proc. Natl. Acad. Sci. USA* 83, 1227–1231.

Vlassov, V. V., Gaidamakov, S. A., Gorn, V. V., Grachev, S. A. (1985b) *FEBS Lett* 182, 415.

Vlassov, V. V., Godovikov, A. A., Kobetz, N. D., Ryte, A. S., Yurchenko, L. V. and Bukrinskaya, A. G. (1985a) *Adv. Enzyme Regulation* 24, 301–320.

Wallace, R. B., Shaffer, J., Murphy, R. F., Bonner, J., Hirose, T. and Itakura, K. (1979) *Nucleic Acids Res.* 6, 3543.

Werner, C., Krebs, B., Keith, G. and Dirheimer, G. (1976) *Biochim. Biophys. Acta* 432, 161.

Wintermeyer, W. and Zachau, H. G. (1973) *Biochim. Biophys. Acta* 299, 82.

Youngquist, R. S. and Dervan, P. B. (1985) *J. Am. Chem. Soc.* 107, 5528.

Zamecnik, P. C. and Stephenson, M. L. (1978) *Proc. Natl. Acad. Sci. USA* 75, 280.

Zarytova, V. F., Kutyavin, I. V., Sil'nikov, V. N., Shishkin, G. V. (1986) *Bioorg. Khim* 12, 911–920.

Zarytova, V. F., Kutyavin, I. V., Sil'nikov, V. N. and Shishkin, G. V. (1986) *Bioorg. Khim.* 12, 911.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A compound of the formula:

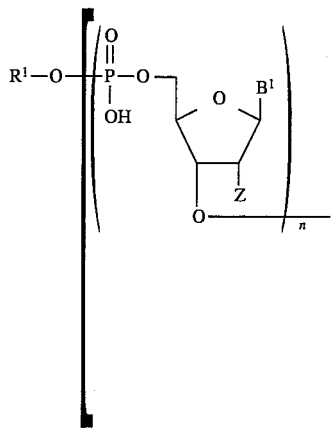

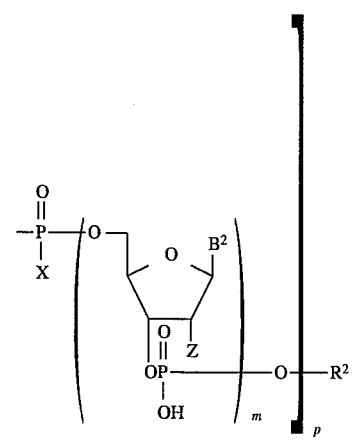

wherein:

$R^1$ and $R^2$ are each H $B^1$ and $B^2$ are each thymine,

X is $NH(CH_2)_3CH_3$,

Z is OH and n, m, p are each 1.

* * * * *